United States Patent [19]

Carson et al.

[11] Patent Number: 5,679,647

[45] Date of Patent: *Oct. 21, 1997

[54] METHODS AND DEVICES FOR IMMUNIZING A HOST AGAINST TUMOR-ASSOCIATED ANTIGENS THROUGH ADMINISTRATION OF NAKED POLYNUCLEOTIDES WHICH ENCODE TUMOR-ASSOCIATED ANTIGENIC PEPTIDES

[75] Inventors: Dennis A. Carson, Del Mar; Eyal Raz, San Diego, both of Calif.

[73] Assignee: The Regents of the University of California, Alameda, Calif.

[*] Notice: The portion of the term of this patent subsequent to Nov. 1, 2014, has been disclaimed.

[21] Appl. No.: 334,260

[22] Filed: Nov. 3, 1994

Related U.S. Application Data

[63] Continuation-in-part of Ser. No. 112,440, Aug. 26, 1993, abandoned.

[51] Int. Cl.[6] .................. A61K 48/00; C12N 15/12; C12N 15/52
[52] U.S. Cl. .................. 514/44; 424/184.1; 536/23.1
[58] Field of Search .................. 514/44; 424/198.1, 424/184.1; 536/23.1

[56] References Cited

U.S. PATENT DOCUMENTS

| | | | |
|---|---|---|---|
| 5,580,859 | 12/1996 | Felgner et al. ............................ | 514/44 |
| 5,589,466 | 12/1996 | Felgner et al. ............................ | 514/44 |

FOREIGN PATENT DOCUMENTS

WO 90/11092  10/1990  WIPO.

OTHER PUBLICATIONS

Chien, "Mucosal Drug Delivery: Potential Routes for Non-invasive Systemic Administration," *Novel Drug Delivery Systems*, vol. 50, pp. 197–227.

Chien, "Transdermal Drug Delivery and Delivery Systems," *Novel Drug Delivery Systems*, vol. 50, pp. 301–380.

Chien, "Nasal Drug Delivery and Delivery Systems," *Novel Drug Delivery Systems*, vol. 50, pp. 229–268.

Sloan, "Use of Solubility Parameters from Regular Solution Theory to Describe Partitioning–Driven Processes," *Prodrugs: Topical and Ocular Drug Delivery*, vol. 53, pp. 179–204.

Tice, et al., "Parenteral Drug Delivery: Injectables," *Treatise on Controlled Drug Delivery*, pp. 315–339.

Chang, et al., "Nasal Drug Delivery," *Treatise on Controlled Drug Delivery*, pp. 423–463.

Been, et al., "One Binding Site Determines Sequence Specificity of Tetrahymena Pre–rRNA Self Splicing, Trans–Splicing, and RNA Enzyme Activity," *Cell*, vol. 47, 207–216, Oct. 24, 1986.

Gillies, et al., "Expression of Human Anti–Tetanus Toxoid Antibody in Transfected Murine Myeloma Cells," *Bio/Technology*, vol. 7, Aug. 1989, pp. 799–804.

Ward et al., "Binding activities of a repertoire of single immunoglobulin variable domains secreted from *Escherichia coli*", *Nature*, vol. 341, 12 Oct. 1989, pp. 544–546.

Wolff, et al., "Conditions Affecting Direct Gene Transfer into Rodent Muscle In Vivo", *BioTechniques* vol. 11, No. 4 (1991), pp. 474–485.

Cohen, "Naked DNA Points Way to Vaccines," *Science*, vol. 259, 19 Mar. 1993, pp. 1691–1692.

Acsadi, et al., "Human dystrophin expression in mdx mice after intramuscular injection of DNA constructs," *Nature*, vol. 352, 29 Aug. 1991, pp. 815–818.

Wolff, et al., "Indirect Gene Transfer into Mouse Muscle in Vivo," *Science*, vol. 24, Mar. 1990, pp. 1465–1468.

Barr, et al., "Systemic Delivery of Recombinant Proteins by Genetically Modified Myoblasts," *Science*, vol. 254, Dec. 1991, pp. 1507–1512.

Ulmer, et al., "Heterologous Protection Against Influenza by Injection of DNA Encoding a Viral Protein," *Science*, vol. 259, 19 Mar. 1993, pp. 1745–1748.

"The Ultimate Delivery System: Lectro Patch Instructions," Advertisement by General Medical Company.

Kaplan, et al., "Rational Immunotherapy with Interleukin 2," *Bio/Technology*, vol. 10, Feb. 1992, pp. 157–162.

Caligiuri, et al., "Selective Modulation of Human Natural Killer Cells In Vivo After Prolonged Infusion of Low Dose Recombinant Interleukin 2," *J. Clin. Invest.*, vol. 91, Jan. 1993, pp. 123–132.

Teppler, et al., "Prolonged Immunostimulatory Effect of Low–Dose Polyethylene Glycol Interleukin 2 in Patients with Human Immunodeficiency Virus Type 1 Infection," *J. Exp. Med.*, vol. 177, Feb. 1993, 483–492.

Lotz, et al., Brief Definitive Report, *J. Exp. Med.*, vol. 167, Mar. 1988, 1253–1258.

Robinson, et al., "Use of Direct DNA Inoculations to Elicit Protective Immune Responses," *Journal of Cellular Biochemistry*, Supp. 17D, 1993, p. 92.

Donohue, et al., "In Vivo Administration of Purified Jurkat–derived Interleukin 2 in Mice," *Cancer Research*, vol. 44, Apr. 1984, pp. 1380–1386.

Goldstein, et al., "Repetitive Weekly Cycles of Interleukin 2: Effect of Outpatient Treatment with a Lower Dose of Interleukin 2 . . . ," *Cancer Research*, vol. 49, pp. 6832–6839, Dec. 1, 1989.

Hefeneider, et al., "In Vivo Interleukin 2 Administration Augments the Generation of Alloreactive Cytolytic T Lymphocytes and Resident Natural Killer Cells," *Journal of Immunology*, vol. 130, No. 1, Jan. 1983, 222–227.

Stribling, et al., "Aerosol gene delivery in vivo," *Proc. Natl. Acad. Sci. USA*, vol. 89, pp. 11277–11281 Dec. 1992.

Del Rey, et al., "Antidiabetic effects of interleukin 1," *Proc. Natl. Acad. Sci. USA*, vol. 86, pp. 5943–5947, Aug. 1989.

Shields, et al., "Calorie restriction suppresses subgenomic mink cytopathic focus–forming murine leukemia virus transcription and frequency . . . ," *Proc. Natl. Acad. Sci. USA*, vol. 88, pp. 11138–11142, Dec. 1991.

Tang, et al., "Genetic immunization is a simple method for eliciting an immune response," *Nature*, vol. 356, 12 Mar. 1992, pp. 152–154.

Gorman, et al., "The Rous sarcoma virus long terminal repeat is a strong promoter when introduced into a variety of eukaryotic cells . . . ," *Proc. Natl. Acad. Sci. USA*, vol. 79, pp. 6777–6781, Nov. 1982.

Norton, et al., "Bacterial B–Galactosidase as a Marker of Rous Sarcoma Virus Gene Expression and Replication," *Molecular and Cellular Biology*, vol. 5, No. 2, Feb. 1985, pp. 281–290.

Krieg, et al., "Functional messenger RNAs are produced by SP6 in vitro transcription of cloned cDNAs," Nucleic Acids Research, IRL Press Limited, vol. 12, No. 18, 1984, pp. 7057–7070.

Huang, et al., "Role of Bone Marrow–Derived Cells in Presenting MHC Class 1–Restricted Tumor Antigens," *Science*, vol. 264, 13 May 1994, pp. 961–965.

Shastri, et al., "Endogenous Generation and Presentation of the Ovalbumin Peptide/$K^b$ Complex to T Cells," *Journal of Immunology*, vol. 150, No. 7, pp. 2724–2736, Apr. 1, 1993.

Liang, et al., "Differential Display of Eukaryotic Messenger RNA by Means of the Polymerase Chain Reaction," *Science*, vol. 257, 14 Aug. 1992, pp. 967–971.

Lisitsyn, et al., "Cloning the Differences Between Two Complex Genomes," *Science*, vol. 259, 12 Feb. 1993, pp. 946–951.

Israeli, et al., "Expression of the Prostate–specific Membrane Antigen," *Cancer Res.*, 54:1807–1811 (1994).

Mamula, et al., "B Cells Process and Present Lupus Autoantigens that Initiate Autoimmune T Cell Responses," *Journal of Immunology*, 1994, 152:1453–1461.

Mader, et al., "A steroid–inducible promoter for the controlled overexpression f cloned genes in eukaryotic cells," *Proc. Natl. Acad. Sci. USA*, vol. 90, pp. 5603–5607, Jun. 1993.

Ferrara, et al., "Highly Potent Transcriptional Activation by 16–ene Derivatives of 1,25–Dihydroxyvitamin $D_3$ ,", *Journal of Biological Chemistry*, vol. 269, No. 4, Jan. 18, 1994, pp. 2971–2981.

*Primary Examiner*—Frank C. Eisenschenk
*Attorney, Agent, or Firm*—Fish & Richardson P.C.

[57] ABSTRACT

The invention is directed to methods for introducing biologically active peptides into a host by administration of polynucleotides which operatively encode for the peptide of interest. In a preferred embodiment of the invention, a host who has been identified as having a tumor bearing at least one tumor-associated antigen is the recipient of a polynucleotide which operatively encodes for a foreign mimic of the tumor-associated antigen or a mutation of the self-antigen. The antigen-encoding polynucleotides are administered to host tissues which have a high concentration of antigen presenting cells in them relative to other host tissues. The method is particularly useful in treating cancer through induction of antigen-specific cytotoxic T lymphocytes in the host for lysis of tumor cells bearing the antigen. Devices and compositions for use in the methods of the invention are also described.

11 Claims, 18 Drawing Sheets

METHODS AND DEVICES FOR IMMUNIZING A HOST AGAINST TUMOR-ASSOCIATED ANTIGENS THROUGH ADMINISTRATION OF NAKED POLYNUCLEOTIDES WHICH ENCODE TUMOR-ASSOCIATED ANTIGENIC PEPTIDES

RELATED PATENT APPLICATIONS

This is a continuation-in-part of PCT application Ser. No. US94/09661, filed Aug. 25, 1994 (designating the U.S. as an elected state), which is in turn a continuation-in-part of U.S. Ser. No. 08/112,440, filed in the United States Patent and Trademark Office on Aug. 26, 1993, now abandoned.

STATEMENT OF GOVERNMENT RIGHTS

This invention may have been made with Government support under Grant Nos. AR07567 and AR25443, awarded by the National Institutes of Health. The Government may have certain rights in this invention.

BACKGROUND OF THE INVENTION

1. Field of the Invention

This invention relates to methods for administering biologically active peptides to a mammalian host by the introduction thereto of one or more polynucleotides to operatively encode for the peptides, preferably by non-invasive means. It also relates to the administration of said polynucleotides to immunize a host against one or more antigens. In particular, the invention relates to the immunization of a host against one or more organ-specific, tumor associated antigens (and eliminating T lymphocyte tolerance thereto) for treatment of malignancies.

2. Description of Related Art

The direct introduction of a biologically active peptide or protein into the cells of a patient can have significant therapeutic value. However, this approach also has several drawbacks. Of primary concern is the risk of potential toxicities, particularly at dosages sufficient to produce a biological response to the peptide. From a practical perspective, there is also the problem of the cost associated with isolating and purifying or synthesizing the peptides. Moreover, the clinical impact of the peptides is also limited by their relatively short half-life in vivo which usually results from their degradation by any proteases present in the target tissue.

For these reasons, introduction of a protein into a patient by delivery of a gene which will express the protein in the patient/host is an intriguing alternative to administering the protein.

In 1984, work at the NIH was reported which showed that intrahepatic injection of naked, cloned plasmid DNA for squirrel hepatitis into squirrels produced both viral infection and the formation of antiviral antibodies in the squirrels (Seeger, et al., *Proc. Nat'l. Acad. Sci USA*, 81:5849–5852, 1984). Several years later, Felgner, et al., reported that they obtained expression of protein from "naked" polynucleotides (i.e., DNA or RNA not associated with liposomes or a viral expression vector) injected into skeletal muscle tissue (Felgner, et al., *Science*, 247:1465, 1990; see also, PCT application WO 90/11092). Felgner, et al. surmised that muscle cells efficiently take up and express polynucleotides because of the unique structure of muscle tissue, which is comprised of multinucleated cells, sarcoplasmic reticulum and a transverse tubular system which extends deep into the muscle cell.

Although it has been supposed that cells of other tissues may also be able to take up naked polynucleotides, expression in other tissues has only been identified to date when delivery of the expressed gene was via a delivery system, e.g., liposomal transformation of the cells. Indeed, other researchers have suggested that uptake and expression of naked polynucleotides in tissues other than skeletal muscle does not occur at detectable or biologically active levels (see, e.g., Stribling, et al., *Proc. Natl. Acad. Sci. USA*, 89:11277–11281, 1992 [expression following aerosol delivery of a gene occurred with use of a liposomal delivery system but not with introduction of DNA alone]; and, Tang, et al., *Nature*, 356:152–154, 1992 [injection with a vaccine "gun" of an hGH plasmid coupled to colloidal gold beads into the skin of mica did not elicit an immune response]).

Although generally effective for gene expression within muscle cells, injection of DNA or RNA into muscle tissue for long-term therapy requires use of repeated injections to offset loss of expression from gene degradation. This approach may not only be time-consuming and expensive, but may also be impractical due to inflammation caused at and near the site of injection. Such inflammation can cause muscle or other somatic cells into which nucleotides are introduced to be themselves targeted by an immune response (see, e.g., Example I) and can lead to severe myonecrosis. Further, intramuscular injection of DNA not only risks injury to muscle tissue, but that injury apparently also compromises the efficacy of the therapy. For example, researchers working with the University of Ottawa recently observed that "[s] triated muscle is the only tissue found to be capable of taking up and expressing reporter genes that are transferred in the form of plasmid DNA . . . but our findings indicate that fibers damaged by the injection procedure do not take up and express plasmid DNA." (Davis, et al, *Human Gene Therapy*, 4:151–159, 1993).

Further, while use of intramuscular injections may be effective on at least a short term basis in therapies directed to disease in the muscle tissue itself, it is likely to be less effective in stimulating a tissue specific immune or other biological response to the expressed peptide elsewhere in the patient's body. As a result, intramuscular injection is not a particularly viable route for achieving expression of peptides at the primary entry points for many infections; i.e., skin and mucosa.

Further, it appears that intramuscular injections of polynucleotides will lead to the formation of both antibodies and cytotoxic T cells in the tissue, due to release of any encoded protein by targeted muscle cells. In contrast, injection of protein (e.g., in a vaccination scheme) does not usually induce cytotoxic T cell formation because exogenous proteins do not efficiently enter the class I processing pathway.

In PCT application WO 90/11092 (discussed supra), the inventors propose that the injection of naked DNA into skeletal muscle or other somatic tissues will lead to direct gene expression in the cytoplasm of the injected cells. The inventors further suppose that the encoded protein will then enter the class I processing pathway to induce cytotoxic T cell formation (which are necessary for the control of established viral infections and cancers). However, as discussed above, it appears that instead any somatic cell that expresses antigen must first release the antigen into the extracellular space for uptake by antigen presenting cells before a class I restricted cytotoxic T cell response can to the antigen can be induced. This conclusion is supported by recent research regarding antigen presentation where the observation was made that "the priming of an immune response against . . . class I restricted antigen that is expressed exclusively in non-hematopoietic cells involves the transfer of that antigen to a host bone marrow derived cell before its presentation." The authors concluded that "professional" antigen presenting cells (i.e., those whose primary purpose was antigen presentation) were required for induction of the class I MHC restricted cytotoxic T lymphocytes ("CTLs") necessary to the treatment of tumors in cancer (Huang, et al., *Science*, 264:961–965, 1994). Thus, at least one premise on which the method for introduction of genetic material into muscle cells for protein expression of PCT application WO 90/11092 was based may not be accurate.

Use of intramuscular injections can, however, produce relatively high levels of protein expression systemically prior to degradation of the injected gene. While this response is desirable in therapies where protein replacement is the goal, it can lead to unintended toxicities in immunization protocols where relatively rapid clearance or lower levels of expression are optimal. As a result, introduction of the gene into tissues which regularly shed or regenerate (such as skin) and/or into cells with a relatively high attrition rate in vivo (such as antigen presenting cells) would be more useful routes for gene immunization.

With respect to delivery systems for genes, means such as viral vectors which introduce the gene into the host's genome present potential health risks association with damage to the genetic material in the host cell. Use of cationic liposomes or a biolistic device (i.e., a vaccine "gun" which "shoots" polynucleotides coupled to beads into tissue) to deliver genes in vivo is preparation intensive and requires some experimentation to select proper particle sizes for transmission into target cells. Further, any invasive means of introducing nucleotides (e.g., injection) poses problems of tissue trauma (particularly in long-term therapies) and presents limited access to certain target tissues, such as organs.

Means for non-invasive delivery of pharmaceutical preparations of peptides, such as iontophoresis and other means for transdermal transmission, have at least the advantage of minimizing tissue trauma. However, it is believed that the bioavailability of peptides following transdermal or mucosal transmission is limited by the relatively high concentration of proteases in these tissues. Yet unfortunately, reliable means of delivering peptides (such as tumor associated antigens) by transdermal or mucosal transmission of genes encoding for them has been unavailable.

The potential benefits of successful administration of peptides via in vivo expression of naked polynucleotides can be illustrated by comparison to the present state of allergen immunotherapy wherein so-called "tumor antigens" are administered to a patient to treat cancer.

Conventional cancer immunotherapy methods have generally failed in inducing a CTL response sufficient to effectuate recovery from a malignancy. Most such approaches have involved injection into the patient of killed, chemically modified cancer cells in adjuvant (see, Quan, et al., *Cancer Treat. Res.*, 65:257–277, 1993). Problematically, the exogenous protein antigens present in such cells are ingested by antigen presenting cells and enter lysosomal vesicles, such that protein antigen based cancer vaccines cannot induce class I restricted immune responses.

Another major obstacle to the development of an efficacious method for protein vaccine based cancer immunotherapy lies in the lack of knowledge concerning the identify of "true tumor antigens"; i.e., antigens which are associated only with cells of a tumor and none other. To date, no such true tumor antigens have been identified. Rather, most purported tumor antigens are either embryonic proteins that have been re-expressed by transformed cells or autoantigens that are not truly tumor specific.

More recent attempts at cancer immunotherapy have sought to stimulate expression of immunostimulatory cytokine encoding genes in cancer cells. However, introduction of cytokine genes into cancer cells has been shown to enhance their capacity to stimulate secondary immune responses, but cannot substitute for the initial function of antigen processing and presentation performed by professional antigen presenting cells. Thus, except for a minority of patients suffering from malignant melanoma, cytokine-based immunotherapy has not succeeded in achieving effective treatment of malignancies (see, e.g., Pandoll, *Curr. Opin. Immunol.*, 5:719–725, 1993).

CTLs which have developed as class I restricted lymphocytes lyse target cells that express "foreign" peptides bound to their class I MHC molecules. The primary function of class I MHC molecules is apparently to act as conduits for display of endogenous proteins on the surface of APCs as peptide/MHC ligands for appropriate T cell receptors. The display of endogenous peptide/MHC complexes on cell surfaces is essential for targeting lytic activity of CTLs specifically to cells which synthesize new intracellular proteins after viral infection or tumorigenic transformation of cells, as well as for deleting-self-reactive T cells in the thymus (see, e.g., Shastri and Gonzalez, *J. Immunol.*, 150:2724–2736, 1993). However, as indicated elsewhere above, recent evidence suggests that primary T lymphocyte immune responses can only be induced by professional antigen presenting cells. Furthermore, the generation of a class I restricted cytotoxic T lymphocyte response usually requires that the antigen be expressed in the cytoplasm of a cell; i.e., of an antigen presenting cell (Huang, et al., supra at p. 964). Such intracellular expression and antigen presentation is not effectively acheived by extracellular administration of a tumor associated antigen to a host (as in the method described by Quan, et al., supra), nor would it be effectively achieved by introduction of a tumor-associated antigen-encoding polynucleotide into tissue cells, such as muscle cells (as in the method proposed by Felgner, et al., *Science*, supra, and in PCT application WO 90/11092).

Another obstacle to cancer immunotherapy based on immunization of the host to tumor associated antigens is tolerance by the host immune system to such antigens. Recent experiments have suggested that T lymphocyte immune tolerance to a self-antigen can be broken by immunizing the host with a mixture of self-antigens and foreign molecular mimics of such antigens (Mamula, et al, *J. Immunol.*, 152:1453–1460, 1994). However, such mixtures fail to induce class I restricted CTL responses in the host because the antigens are expressed extracellularly, rather than in the cytoplasm of APCs.

A need, therefore, exists for a method for treatment of cancer which induces the development of tumor associated antigen-specific class I restricted CTLs. It also suggests a need for a means of introducing a gene encoding for a biologically active peptide to a host in a tissue-specific manner without significant tissue trauma.

The present invention addresses all of these needs.

SUMMARY OF THE INVENTION

The details of the preferred embodiment of the present invention are set forth in the accompanying drawings and the description below. Once the details of the invention are known, numerous additional innovations and changes will become obvious to one skilled in the art.

1. DEFINITIONS

The following definitions are provided to simplify discussion of the invention. Those skilled in the art will, however, recognize that these definitions may be expanded to include equivalents without departing from the legitimate scope or spirit of the invention. For this reason, these definitions should not be construed as limiting the invention.

a. "Naked polynucleotide(s)" refers to DNA or RNA and can include sense and antisense strands as appropriate to the goals of the therapy practiced according to the invention. Polynucleotide in this context may include oligonucleotides. Naked in this context means polynucleotides which are not complexed to colloidal materials (including liposomal preparations), or contained within a vector which would cause integration of the polynucleotide into the host genome.

b. "Operatively encoding" refers to a polynucleotide which has been modified to include promoter and other sequences necessary for expression and, where desired, secretion of the desired translation product; e.g., a peptide or protein. All the embodiments of the invention can be practiced using known plasmid expression vectors. Preferably, these vectors will include cDNA ('s) which encode for the desired translation product. Therefore, unless context otherwise requires, it will be assumed that "polynucleotide" or "naked polynucleotide" refers to operatively encoding sequences contained in a suitable plasmid expression vector, examples of which are provided herein.

c. "Mixture of polynucleotides" shall refer to more than one and up to 200 polynucleotide species which are under the control of the same promoter.

d. "Synthesis" refers to well-known means of synthesizing polynucleotide sequences and may include isolation and purification of native polynucleotides.

e. "Peptide" refers to small peptides, polypeptides, oligopeptides and proteins which have a desired biological effect in vivo.

f. "Iontophoresis" refers to a known means of transdermal transmission presently used to deliver peptides continuously to a host. More specifically, it is a process that facilitates the transport of ionic species by the application of a physiologically acceptable electrical current. This process and other transdermal transmission means are described in Chien, et al. *Transdermal Drug Delivery*, "Novel Drug Delivery Systems", Ch. 7, part C, (Marcel Dekker, 1992), the relevant disclosures of which are incorporated herein by this reference for the purpose of illustrating the state of knowledge in the art concerning techniques for drug delivery.

g. "Detergents/Absorption Promoters" refers to chemical agents which are presently known in the art to facilitate absorption and transfection of certain small molecules, as well as peptides.

h. "Antigen Presenting Cells", or "APC's" include known APC's such as Langerhans cells, veiled cells of afferent lymphatics, dendritic cells and interdigitating cells of lymphoid organs. The definition also includes mononuclear cells such as (1) lymphocytes and macrophages which take up and express polynucleotides according to the invention in skin and (2) mononuclear cells depicted on histological photographs contained herein. These cells are not tissue cells but are likely to be antigen presenting cells. The most important of these with respect to the present invention are those APC's which are known to be present in high numbers in epithelia and thymus dependent areas of the lymphoid tissues, including epidermis and the squamous mucosal epithelia of the buccal mucosa, vagina, cervix and esophagus (areas with "relatively high" concentrations of APC's). In addition to their definitions set forth below, therefore, "skin" and "mucosa" as used herein particularly refer to these sites of concentration of APC's. Further, "professional APCs" shall refer to cells whose primary purpose is antigen presentation; i.e., bone marrow derived cells.

i. "Host" refers to the recipient of the therapy to be practiced according to the invention. The host may be any vertebrate, but will preferably be a mammal. If a mammal, the host will preferably be a human, but may also be a domestic livestock or pet animal.

j. "Target tissue" refers to the tissue of the host in which expression of the naked polynucleotide is sought.

k. "Skin" as used herein refers to the epidermal, dermal and subcutaneous tissues of a host.

l. "Mucosa" refers to mucosal tissues of a host wherever they may be located in the body including, but not limited to, respiratory passages (including bronchial passages, lung epithelia and nasal epithelia), genital passages (including vaginal, penile and anal mucosa), urinary passages (e.g., urethra, bladder), the mouth, eyes and vocal cords.

m. "Point of Entry" refers to the site of introduction of the naked polynucleotide into a host, including immediately adjacent tissue.

n. "Dermal" and "Epidermal Administration" mean routes of administration which apply the naked polynucleotide(s) to or through skin. Dermal routes include intradermal and subcutaneous injections as well as transdermal transmission. Epidermal routes include any means of irritating the outermost layers of skin sufficiently to provoke an immune response to the irritant. The irritant may be a mechanical or chemical (preferably topical) agent.

o. "Epithelial Administration" involves essentially the same method as chemical epidermal administration, except that the chemical irritant is applied to mucosal epithelium.

p. "IL" refers to interleukin.

q. "TH1 Response(s)" refers to a cellular immune response that is induced preferentially by antigens that bind to and activate certain APC's; i.e., macrophages and dendritic cells.

r. "Biologically Active Peptide(s)" refers to a peptide which, when administered to a host, exerts a therapeutic benefit or induces an immune response therein.

s. "Activating Ligand" refers to a ligand which, when bound to a nuclear receptor, induces activity on the part of the receptor.

t. "Tumor-associated Antigen(s)" refers to embryonic proteins that have been re-expressed by transformed cells or autoantigens that are not truly tumor specific, but are present in mammalian tumor tissue.

2. DISCUSSION

In one aspect, the invention consists of means of inducing local immunity to an antigen or a systemic response to a therapeutic peptide or polynucleotide by delivering a naked polynucleotide to a host's cells which operatively encodes the antigen or peptide. More particularly, the naked polynucleotide is preferably delivered to a tissue which contains a relatively high concentration of antigen presenting cells as compared to other tissues of the body. Although it is not intended that the invention will be entirely limited by a particular theory as to the mechanism of expression involved, it is believed that a biological response in these tissues following administration of the naked polynucleotide is achieved because the polynucleotide is expressed intracellularly in the cytoplasm of mononuclear cells, most likely the host's antigen presenting cells. It is also believed that the mononuclear cells may be involved in an inflammatory immune response to the naked polynucleotide once the cells have migrated into the lymph system and presented the expressed peptide as antigen.

Based on histological studies, the naked polynucleotides do not appear to be taken up directly by fibroblasts or other tissue cells in significant quantities (see, Example IV and FIG. 6). This conclusion is borne out by studies showing that (1) intradermal administration of even minute amounts of naked polynucleotides into mice induced a prominent TH1 response (indicative of antigen presentation by macrophages and dendritic cells; see, Example XI and FIGS. 13–14); (2) intradermal administration of naked polynucleotide to mice induced the formation of cytotoxic T cells without stimulating production of detectable levels of antibody (see, Example IX and FIG. 11); and, (3) induction of prolonged immunological memory with respect to the polynucleotide expression product as an antigen (Example X and FIGS. 12–13). It therefore appears that the immunogeneity of naked polynucleotides depends not on the amount of protein expressed thereby, but instead on the type of cell transfected (e.g., antigen presenting cells versus tissue cells).

Given the apparent role of inflammation in this method of the invention, it will also be appreciated by those of skill in the art that increased permeability in cell membranes of the target tissue associated with inflammation may enhance uptake of the naked polynucleotides (particularly across barriers such as skin and mucosa).

Ideally, the target tissue will be skin or mucosa, where approximately 1% to 2% of the cell population is comprised of antigen presenting cells. These tissues are particularly preferred when the therapy is directed to infections or diseases where it is desirable to induce a localized therapeutic or immune response. For example, a mucosal route of administration would be preferred for treatment of sexually transmitted diseases, where the therapy was directed to boosting the immune response to antigens in infected tissues. A nasal route of administration (via inhalation or insufflation) would also be of particular use in therapies directed toward treatment of respiratory and related diseases. The skin and mucosa are also preferred for their regenerative ability, which limits the length of time that introduced materials will remain at the point of entry.

Because the antigen presenting cells present in the target tissue may serve to mediate the expression of the naked polynucelotide, the method of the invention may not be as useful for inducing systemic responses to the expressed peptide as it is for inducing a localized response. However, at sufficient dosage levels a transitory systemic effect can be induced. A useful application of this aspect of the invention for induction of systemic responses to the expressed peptide may, therefore, be as an adjuvant for other systemic therapies.

In another aspect of the invention, the APC's serve as vehicles to deliver the naked polynucelotide to lymphatic organs and to mucosal tissues other than those at the point of entry. This embodiment is illustrated by reference to the following hypothesis; the mechanism described should not, however, be construed as limiting the invention.

In this embodiment, it is believed that the APC's take up the naked polynucelotide at or near the point of entry then carry them into lymphatic circulation. Once at a lymph node, the APC will present the intracellularly expressed protein as an antigen, thereby stimulating an immune response. From there, those APC's which carry "homing" receptors for, e.g., mucosa, may reenter lymphatic circulation until they settle in a target tissue other than the tissue at the point of entry. Where desired, homing receptors (specific membrane proteins which bind to target cell ligands) may be sequenced and incorporated into the naked polynucleotide.

With respect to expression in the lymph system, this embodiment also provides a means of enhancing the host's immune responsiveness by delivering cytokines to increase the concentration of specific cytokines present in the host. Particularly in the lymphatic organs, increases in the host's levels of circulating cytokines (administered with or shortly after antigen challenge) can boost the host's immune response to pathogenic antigens and (1) serve as an adjuvant for vaccines, (2) decrease the immune response to self-antigens in autoimmune diseases, or (3) decrease the immune response to alloantigens (produced, for example, following tissue or organ transplantation).

Where the APC's carrying the gene of interest migrate out of lymph nodes and circulate to tissues for which they have a homing receptor, the gene can be administered at an accessible point of entry for expression at a less convenient or accessible site. For example, a naked polynucelotide delivered intranasally may, under appropriate conditions, be expressed in the genital mucosa.

Another use for the invention would be in moderating an immune response to an antigen (such as a tumor associated antigen) by immunizing the host against the antigen. The skin and nasal routes of administration, particularly the former, are of particular use in this regard.

For use in cancer immunotherapy, the method would preferably involve the following steps:

1. Selection or identification of a tumor-associated antigen of interest and polynucleotide which encodes the antigen.

2. Where the antigen is a self-antigen (as opposed to a tumor-associated antigen from another mammalian species), modification of a polynucleotide which encodes the tumor-associated antigen of interest as a self-antigen to mimic, but not be identical to, the self-antigen. Preferably, the mutation will substitute or delete a single nucleotide corresponding to the region of the self-antigen which is most immunogeneic.

3. Rendering the polynucleotide operatively encoding; i.e., by insertion into a recombinant expression vector.

4. Administration of the operatively encoding polynucleotide as a naked polynucleotide according to the invention.

5. Optionally co-immunizing the host with protein tumor-associated antigen vaccines to stimulate assistance by helper T lymphocytes and/or with cytokine-encoding polynucleotides to enhance the performance of the host's immune system. However, because the development of anti-tumor-associated antigen antibodies will be accompanied by the release of soluble antigen (which poses the risk of interference with CTL activity and of encouraging immune complex disease), the preferred practice of the invention will induce CTLs without inducing antibody formation (by avoiding the extracellular release of soluble antigen).

A related aspect of the above-described method is its use in vitro or in an animal model (preferably a primate or rodent) to screen tumor-associated antigen-encoding polynucleotides mutated according to step 2 for their ability to produce tumor-associated antigen specific CTLs in a host.

Another particular advantage of the invention is that it involves the administration of relatively minute doses of antigen. More specifically, because a polynucleotide that will operatively encode for an antigen is administered in lieu of the antigen itself, the quantity of foreign material being introduced to the host is relatively minimal. Moreover, routes of administration of naked polynucleotides through skin or mucosa require a lower concentration of DNA to produce the same magnitude of immune response than does the intramuscular route of administration (e.g., about 10–50 fold lower; see, e.g., Example X and FIGS. 12–13). As a result, the invention lends itself well to the administration of naked polynucleotides which encode for up to several hundred different antigens for use, as an example, as a polyvalent vaccine.

The preferred routes of administration for inducing local immunity in or near the skin will be by transdermal transmission, intradermal injection or superficially scratching or irritating the outermost layer of epidermal cells (i.e., epidermal administration), although subcutaneous injection may also be of use in certain applications. The preferred routes of administration for inducing local immunity in the respiratory tract will be by inhalation or insufflation; routes of administration to other mucosal tissues will vary according to their location.

Where the naked polynucleotides are to be introduced into skin or mucosa, delivery of the polynucleotide is preferably facilitated without need for injection by use of detergents, absorption promoters, chemical irritants (such as keratinolytic agents), or mechanical irritants. Detergents and absorption promoters which facilitate uptake of small molecules other than genes are well known in the art and may, without undue experimentation, be adapted for use in facilitating uptake of genes. Another substantially noninvasive approach to introducing the naked polynucleotides is by transdermal transmission (preferably iontophoresis) which has been used with success for transdermal transmission of peptides.

For those embodiments of the invention which involve stimulating production of cytokines and related peptides in circulation, use of any parenteral route of administration is possible, although use of routes involving little or no invasion of host tissues are greatly preferred. However, because of the need for repeated administration of the naked polynucleotide(s), intramuscular injections are not preferred. Instead, introduction of the naked polynucleotide(s) to an area of the body which is regenerative, such as skin and mucosa, is preferred for their ability to replace cells which have been directly affected by trauma associated with each dosage. Where desired, to ensure secretion of the proteins to be expressed in these embodiments of the invention, sequences controlling secretion known to those skilled in the art will be included in the administered naked polynucleotide, if not already present in the full-length gene. However, for use in immunizing a host to an antigen, it will be preferable for the antigen not to be secreted by APC's in which it is expressed, but rather presented on the cell surface. Thus, for use in embodiments of the invention which seek to immunize the host to an antigen, the naked polynucleotides will preferably be under the control of sequences which prevent secretion of expressed protein, which sequences are known to those of skill in the art.

Use of liposomes for delivery of the naked polynucleotides of the invention is not preferred. Rather, such use is likely to result in reduced levels of expression. This phenomenon is likely to be the result of impaired recognition by APC's of a liposome as an antigenic material.

DETAILED DESCRIPTION OF THE INVENTION

Figure 1A:
FIG. 1A depicts a section of muscle tissue demonstrating chronic inflammation
Figure 1B:
FIG. 1B depicts a section of muscle tissue displaying myonecrosis following intra-muscular injections of pREVk3 and pRSVIL-2.

Throughout this description, the preferred embodiment and examples shown should be considered as exemplars, rather than limitations on the invention.

I. INTRODUCTION OF NAKED POLYNUCLEOTIDES INTO TARGET TISSUES HAVING SUBSTANTIAL CONCENTRATIONS OF ANTIGEN PRESENTING CELLS

A. Preparation of Naked Polynucleotides

The polynucleotides to be used in the invention may be DNA or RNA, but will preferably be a complementary DNA (cDNA) sequence. The polynucleotide sequences used in the invention must be (a) expressible and (b) either nonreplicating or engineered by means well known in the art so as not to replicate into the host genome. Illustrations of the preparation of polynucleotides suitable for use in the invention follow and specific examples showing how particular polynucleotide compositions were made are provided infra. It will, however, be apparent to those skilled in the art that other known means of preparing nonreplicating polynucleotides may also be suitable.

Polynucleotides for use in the invention can be obtained using hybridization methods well known in the art. DNA and RNA may also be synthesized using automated nucleic acid synthesis equipment well known in the art. Use of the well-known polymerase chain reaction (PCR) is particularly preferred for generating mixtures of polynucleotides. Genomic nucleic acids may be prepared by means well-known in the art such as the protocols described in Ausubel, et al., *Current Protocols in Molecular Biology*, Chs. 2 and 4 (Wiley Interscience, 1989). cDNA can be synthesized according to means well known in the art (see, e.g., Maniatis, et al., *Molecular Cloning*; A Laboratory Manual (Cold Spring Harbor Lab, N.Y., 1982). A cDNA expression library containing polynucleotides of interest can also be screened by means well known in the art. For reference, examples of such means are illustrated by the discussion below.

Preferred polynucleotides for use in specific applications are suggested in the preceding Summary of the Invention. For example, the naked polynucleotides may operatively encode for therapeutic peptides, but will preferably encode for immunogenic peptides which can act as antigens to provoke a humoral and/or cellular response. The naked polynucleotides can also operatively encode for an antibody. In this regard, the term "antibody" encompasses whole immunoglobulin of any class, chimeric antibodies, hybrid antibodies with dual or multiple antigen specificities and fragments including hybrid fragments. Also included within the meaning of "antibody" are conjugates of such fragments, and so-called antigen binding proteins (single chain antibodies) as described, for example, in U.S. Pat. No. 4,704,692. Alternatively, the encoded antibodies can be anti-idiotypic antibodies (antibodies that bind other antibodies) as described, for example, in U.S. Pat. No. 4,699,880.

Those of skill in the art will, however, appreciated that the methods of the invention may be adapted for use in administering any polynucleotide or mixture thereof which operatively encode therapeutic and/or immunogenic peptides of interest. The invention is therefore not limited to use with any particular polynucleotide(s).

As used herein, "polynucleotide" refers to a polymer of deoxyribonucleotides or ribonucleotides, in the form of a separate fragment or as a component of a larger construct. DNA encoding an therapeutic and/or immunogenic peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code, which sequences may be readily determined by those of ordinary skill in the art.

Polynucleotide sequences encoding a desired therapeutic and/or immunogenic peptide can be expressed in either eukaryotes or prokaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are also well known in the art. Such vectors are used to incorporate DNA of the invention.

DNA sequences for use in producing therapeutic and/or immunogenic peptides of the invention can also be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR). The development of specific DNA sequences encoding or fragments thereof, can also be obtained by: 1) isolation of double-stranded DNA sequences from the genomic DNA: 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Hybridization procedures are useful for the screening of recombinant clones by using labeled mixed synthetic oligonucleotide probes where each probe is potentially the complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture.

A cDNA library believed to contain a polynucleotide of interest can be screened by injecting various mRNA derived from cDNAs into oocytes, allowing sufficient time for expression of the cDNA gene products to occur, and testing for the presence of the desired cDNA expression product, for example, by using antibody specific for a peptide encoded by the polynucleotide of interest or by using probes for the repeat motifs and a tissue expression pattern characteristic of a peptide encoded by the polynucelotide of interest. Alternatively, a cDNA library can be screened indirectly for expression of therapeutic and/or immunogenic peptides having at least one epitope using antibodies specific for the peptides. Such antibodies can be either polyclonally or monoclonally derived and used to detect expression product indicative of the presence of cDNA of interest.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

The naked polynucleotides may be conjugated to or used in association with other polynucleotides which operatively code for regulatory proteins that control the expression of these polypeptides or may contain recognition, promoter and secretion sequences. Those of ordinary skill in the art will be able to select regulatory polynucleotides and incorporate them into the naked polynucleotides of the invention (if not already present therein) without undue experimentation. For example, suitable promoters for use in murine or human systems and their use are described in *Current Protocols in Molecular Biology*, supra at Ch. 1.

A particularly preferred form of a naked polynucleotide for use in the invention will be one which has been incorporated into a plasmid vector. Use of a plasmid vector, particularly one which comprises a replicator, will prolong expression of the gene in target tissues. Certain plasmid vectors are also good mediators of immune responses to immunogenic peptides because high levels of expression are achieved when the gene encoding the peptides is incorporated into the vector.

Suitable plasmid vectors are well-known in the art and include the vectors described in *Current Protocols in Molecular Biology*, supra at Ch. 1. Two particularly preferred plasmid vectors are the pRSV (Rous sarcoma virus) and pCMV (cytomegalovirus) promoter vectors. Of these promoters, CMV is preferred for polynucleotides to be introduced into tissue other than muscle. This preference is based on observations that higher levels of expression are achieved in this context when the CMV promoter is employed.

A suitable protocol for isolation of the RSV promotor and its use in construction of a plasmid vector is described in Gorman, et al., *Proc. Natl. Acad. Sci, USA*, 79:6777, (1982). Other preferred plasmid vectors are pREP7 and pREV which are commercially available from Invitrogen of San Diego, Calif. For cloning of polynucleotides, a particularly suitable plasmid for production of mRNA is the pSP64T cloning vector described by Kreig, et al., *Nucleic Acids Res.*, 12:7057–7070, (1984). Any cDNA containing an initiation codon can be introduced into this plasmid and mRNA prepared from the expressed DNA templates using conventional techniques.

A particularly useful vector for administration of any naked polynucleotides according to the invention are those which contain a promoter that can be switched "on" or "off" after the vector has been administered to the patient.

Particularly efficacious examples of such promoters are the ligand inducible nuclear receptor promoters. Nuclear receptors represent a family of transcriptional enhancer factors that act by binding to specific DNA sequences found in target promoters known as response elements. Specific members of the nuclear receptor family include the primary intracellular targets for small lipid-soluble ligands, such as vitamin $D_3$ and retinoids, as well as steroid and thyroid hormones ("activating ligands").

Nuclear receptors activated by specific activating ligands are well suited for use as promoters in eukaryotic expression vectors since expression of genes can be regulated simply by controlling the concentration of ligand available to the receptor. For example, glucocorticoid-inducible promoters such as that of the long terminal repeat of the mouse mammary tumor virus (MMTV) have been widely used in this regard because the glucocorticoid response elements are expressed in a wide variety of cell types. One expression system which exploits glucocorticoid response elements responsive to a wide variety of steroid hormones (e.g., dexamethasone and progesterone) is a pGREtk plasmid (containing one or more rat tyrosine amino transferase glucocorticoid response elements upstream of the herpes simplex virus thymidine kinase (tk) promoter in pBLCAT8+), transfected in HeLa cells (see, Mader and White, *Proc. Natl. Acad. Sci USA*, 90:5603–5607, 1993 [pGRE2tk]; and, Klein-Hitpass, et al., *Cell*, 46:1053–1061, 1986 [pBLCAT8+]; the disclosures of which are incorporated herein by this reference to illustrate knowledge in the art concerning construction of suitable promoters derived from nuclear receptor response elements ["NRRE promoters"]). The pGREtk promoter (see, map at FIG. 20) is particularly effective in stimulating controlled overexpression of cloned genes in eukaryotic cells (Mader and White, supra at 5607).

Another particularly suitable NRRE promoter for use in the invention is one which is inducible by the vitamin $D_3$ compound 1,25-dihydroxyvitamin $D_3$ and non-hypercalcemic analogs thereof (collectively, "vitamin $D_3$ activating ligands"). NRRE promoters inducible by vitamin $D_3$ activating ligands contain the vitamin $D_3$ receptor (VDR) response elements PurG(G/T)TCA which recognizes direct repeats separated by 3 base pairs. Vitamin $D_3$ response elements are found upstream of human osteocalcin and mouse osteopontin genes; transcription of these genes is activated on binding of the VDR (see, e.g., Morrison and Eisman, *J. Bone Miner. Res.*, 6:893–899, 1991; and, Ferrara, et al., *J. Biol Chem.*, 269:2971–2981, 1994, the disclosures of which are incorporated herein by this reference to illustrate knowledge in the art of vitamin $D_3$ responsive inducible promoters). Recent experimental results from testing of a recombinant expression vector containing the mouse osteopontin VDR upstream of a truncated herpes simplex virus thymidine kinase (tk) promoter suggested that 9-cis-retinoic acid can augment the response of VDR to 1,25-hydroxyvitamin $D_3$ (see, Carlberg, et al., *Nature*, 361:657–660, 1993).

Figure 21:
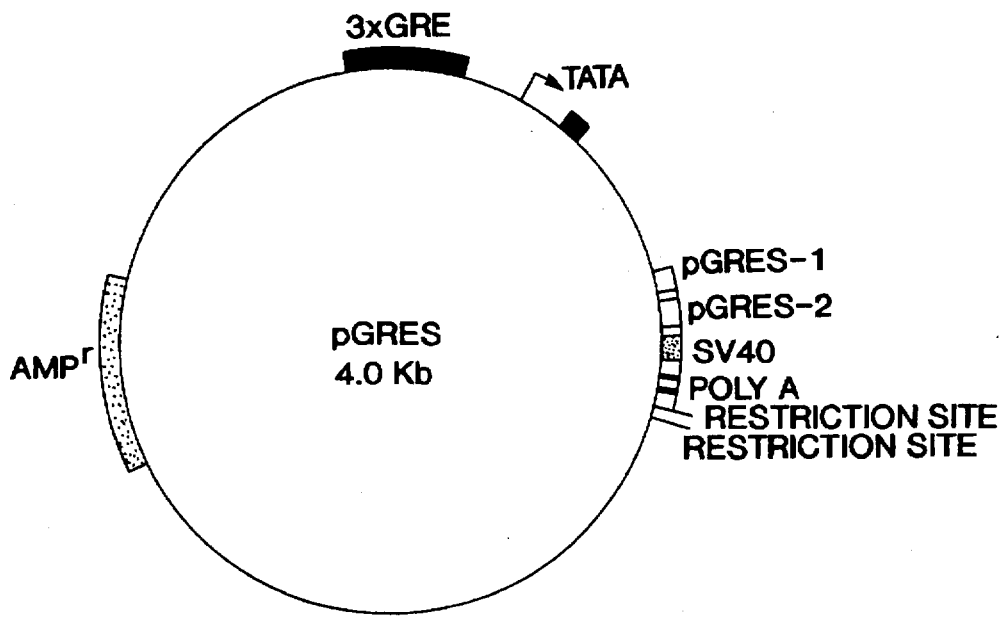
FIG. 21 is a map of the pGREtk eukaryotic expression vector.
Figure 22:
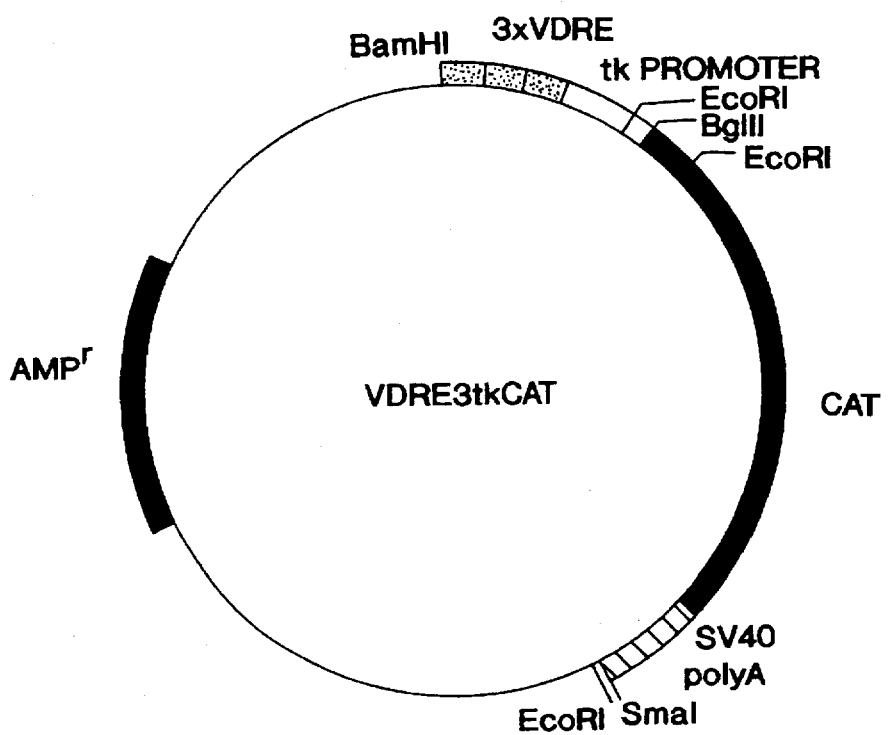
FIG. 22 is a map of the pVDRtk eukaryotic expression vector.

Ferrara, et al. also described vitamin $D_3$ inducible promoters in recombinant expression vectors constructed using multiple copies of a strong VDR; in particular, the mouse osteopontin VDR (composed of a direct repeat of PurGT-TCA motifs separated by 3 base pairs). This VDR conforms to the PurGG/TTCA consensus motifs which have previously been shown to be responsive not only to vitamin $D_3$, but also to thyroid hormone and/or retinoic acid. As many as three copies of the mouse VDR was inserted into pBLCAT8+; immediately upstream of the herpes simplex virus tk promoter (see, e.g., FIG. 21 [map of pVDREtk]). Transfection of the resulting VDREtk vector into COS cells (producing a "VDR expression system") proved to be particularly useful in that COS cells contain the nuclear retinoid X receptor (RXR) that has been shown to act as an auxiliary factor for binding of VDR to its response element.

The VDR expression system (and functionally equivalent expression systems under the control of, for example, human osteocalcin gene promoter) is uniquely suited for use in the invention. Specifically, expression of a naked polynucleotide administered to a mammal according to the invention by epidermal or dermal routes (particularly the former) in a vitamin $D_3$ responsive expression system can be switched on by topical administration of a 1,25-dihydroxyvitamin $D_3$ preparation at the point of entry (and off by withdrawing the vitamin $D_3$ preparation and/or modulated by applying or withdrawing a source of retinoic acid to or from the point of entry). Conveniently, 1,25-dihydroxyvitamin $D_3$ and non-hypercalcemic analogs thereof have been approved for use in topical preparations by the United States Food and Drug Administration for the treatment of psoriasis and are commercially available.

In vivo tests of the NRRE promoters indicate that they are inducible on systemic exposure to their corresponding response elements (see, Tsou, et al. *Exp. Cell Res.*, 214:27–34, 1994). Given the expected retention of polynucleotides administered dermally or epidermally at the point of entry (thus making them available for exposure to topically absorbed response elements; see, e.g., discussion at pages 15–16 and data in Example IV), it can be reasonably predicted that use of NRRE promoters for expression of such polynucleotides will also permit their in vivo control through topical administration of appropriate NRRE promoter activating ligands (e.g., 1,25-dihydroxyvitamin $D_3$ transcriptional activators with a VDR expression vector for expression of the polynucleotide of interest).

Thus, use of an NRRE promoter recombinant expression vector for administration and expression of naked polynucleotides according to the invention permits control of expression to, for example, switch on expression when dosing is needed or switch off expression in the event of an adverse reaction to the expressed protein or peptide.

Various viral vectors that can be utilized (albeit are not preferred for use) in the invention include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated.

By inserting one or more sequences of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the polynucleotides of interest. A separate vector can be utilized for targeted delivery of a replacement gene to the cell(s), if needed. In antisense therapy, an antisense oligonucleotide and the replacement gene may also be delivered via the same vector since the antisense oligonucleotide is specific only for target gene containing a polymorphism.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence that enables the packaging mechanism to recognize an RNA transcript for encapsidation. Helper cell lines that have deletions of the packaging signal include, but are not limited to, $\psi$2, PA317 and PA12, for example. These cell lines produce empty virions, since no genome is packaged. If a retroviral vector is introduced into such helper cells in which the packaging signal is intact, but the structural genes are replaced by other genes of interest, the vector can be packaged and vector virion can be produced.

For purposes of monitoring expression, these vectors may be modified to include known reporter genes. For example, the pRSV lac-Z DNA vector described in Norton, et al., *Mol. Cell. Biol.*, 5:281, (1985), may produce $\beta$-galactosidase which protein expression. Luciferase and chloramphenicol acetyl transferase ("CAT"; see, e.g., Gorman, et al., supra, re construction of a pRSV-CAT plasmid) may also be used. Convenient plasmid propogation may be obtained in *E. coli* (see, e.g., *Molecular Cloning: A Laboratory Manual*, supra.)

For use as a tolerizing vaccine, a mixture of polynucleotides or separately coadministered group of polynucleotides may include a gene operatively encoding for an immunosuppressive cytokine (such as TGF$\beta$) and a separate gene operatively encoding for a relevant histocompatibility protein. This approach could be adapted for use in inducing tolerance to foreign antigens (including alloantigens) as well as self-antigens.

B. Pharmaceutical Preparations of Naked Polynucleotides

Compositions of naked polynucleotides and mixtures of polynucleotides may be placed into a pharmaceutically acceptable suspension, solution or emulsion. Suitable mediums include saline and may, for those embodiments which do not rely on antigen presenting cells for delivery of the polynucleotides into target tissue, liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of naked polynucleotides may be lyophilized using means well known in the art, for subsequent reconstitution and use according to the invention.

For those embodiments of the invention which do not rely on APC recognition of naked polynucleotides as antigen, in addition to the targeted vector delivery systems discussed supra, a colloidal dispersion system may also be used for targeted delivery. However, it will be appreciated by those of skill in the art that the advantages of employing the method of the invention to administer naked nucleotides, and of administering those nucleotides to tissues having relatively high concentrations of antigen presenting cells, are such that the use of collodidal dispersion systems for delivery of polynucleotides will not be a preferred method. The discussion below regarding such systems is therefore provided principally for reference in the event that the preferred method of the invention is determined to be unavailable for use with respect to a particular indication.

Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

For those embodiments of the invention which do rely on APC expression, liposomal preparations substantially limit uptake of the naked polynucleotides in vivo and should not be used. Instead, isotonic buffered solution is the preferred medium for maximal uptake of the naked polynucleotides in such embodiments. Further, use of absorption promoters, detergents, chemical irritants or mechanical irritation means is also preferred to enhance transmission of the naked polynucleotide composition through the point of entry. For reference concerning general principles regarding promoters and detergents which have been used with success in mucosal delivery of organic and peptide-based drugs, see Chien, *Novel Drug Delivery Systems*, Ch. 4 (Marcel Dekker, 1992). Specific information concerning known means and principles of nasal drug delivery are discussed in Chien, supra at Ch 5. Examples of suitable nasal absorption promoters are set forth at Ch. 5, Tables 2 and 3; milder agents are preferred. Further, known means and principles of transdermal drug delivery are also discussed in Chien, supra, at Ch. 7. Suitable agents for use in the method of this invention for mucosal/nasal delivery are also described in Chang, et al., *Nasal Drug Delivery*, "Treatise on Controlled Drug Delivery", Ch. 9 and Table 3–4B thereof, (Marcel Dekker, 1992). Suitable agents which are known to enhance absorption of drugs through skin are described in Sloan, *Use of Solubility Parameters from Regular Solution Theory to Describe Partitioning-Driven Processes*, Ch. 5, "Prodrugs: Topical and Ocular Drug Delivery" (Marcel Dekker, 1992), and at places elsewhere in the text.

It is expected that these techniques (and others which are conventionally used to facilitate drug delivery) may be adapted to preparation of naked polynucleotides for use in the methods of the invention by those of ordinary skill in the art without undue experimentation. In particular, although the approaches discussed in the preceding paragraphs have not, to the inventors' knowledge, been previously used for polynucleotide delivery, it is believed that they are suitable for use to that end. For that reason, the references identified above, while not essential to the inventive methods, are incorporated herein by this reference. Specific examples illustrating this suitability are set forth infra.

C. Means For, And Routes Of, Administration of Naked Polynucleotides

For dermal routes of administration, the means of introduction may be by epidermal administration, subcutaneous or intradermal injection. Of these means, epidermal administration is preferred for the greater concentrations of APC's expected to be in intradermal tissue.

The means of introduction for dermal routes of administration which are most preferred, however, are those which are least invasive. Preferred among these means are transdermal transmission and epidermal administration.

For transdermal transmission, iontophoresis is a suitable method. Iontophoretic transmission may be accomplished using commercially available "patches" which deliver their product continuously through unbroken skin for periods of several days or more. Use of this method allows for controlled transmission of pharmaceutical compositions in relatively great concentrations, permits infusion of combination drugs and allows for contemporaneous use of an absorption promoter.

An exemplary patch product for use in this method is the LECTRO PATCH trademarked product of General Medical Company of Los Angeles, Calif. This product electronically maintains reservoir electrodes at neutral pH and can be adapted to provide dosages of differing concentrations, to dose continuously and/or to dose periodically. Preparation and use of the patch should be performed according to the manufacturer's printed instructions which accompany the LECTRO PATCH product; those instructions are incorporated herein by this reference.

Epidermal administration essentially involves mechanically or chemically irritating the outermost layer of the epidermis sufficiently to provoke an immune response to the irritant. Specifically, the irritation should be sufficient to attract APC's to the site of irritation. As discussed previously, it is believed that the APC's then take up and express the administered naked polynucleotide.

An exemplary mechanical irritant means employs a multiplicity of very narrow diameter, short tynes which can be used to irritate the skin and attract APC's to the site of irritation, to take up naked polynucleotides transferred from the end of the tynes. For example, the MONO-VACC old tuberculin test manufactured by Pastuer Merieux of Lyon, France contains a device suitable for introduction of naked polynucleotides.

The device (which is distributed in the U.S. by Connaught Laboratories, Inc. of Swiftwater, Pa.) consists of a plastic container having a syringe plunger at one end and a tyne disk at the other. The tyne disk supports a multiplicity of narrow diameter tynes of a length which will just scratch the outermost layer of epidermal cells. Each of the tynes in the MONO-VACC kit is coated with old tuberculin; in the present invention, each needle is coated with a pharmaceutical composition of naked polynucleotide or a mixture thereof. Use of the device is according to the manufacturer's written instructions included with the device product; these instructions regarding use and administration are incorporated herein by this reference to illustrate conventional use of the device. Similar devices which may also be used in this embodiment are those which are currently used to perform allergy tests.

Another suitable approach to epidermal administration of naked polynucleotides is by use of a chemical which irritates the outermost cells of the epidermis, thus provoking a sufficient immune response to attract APC's to the area. An example is a keratinolytic agent, such as the salicylic acid used in the commercially available topical depilatory creme sold by Noxema Corporation under the trademark NAIR. This approach may also be used to achieve epithelial administration in the mucosa. The chemical irritant may also be applied in conjunction with the mechanical irritant (as, for example, would occur if the MONO-VACC type tyne were also coated with the chemical irritant). The naked polynucleotide may be suspended in a carrier which also contains the chemical irritant or coadministered therewith.

For mucosal administration, the means of introduction will vary according to the location of the point of entry. Particularly for immunization to and treatment of respiratory infections, intranasal administration means are most preferred. These means include inhalation of aerosol suspensions or insufflation of the naked polynucleotide or mixtures thereof. Suppositories and topical preparations will also be suitable for introduction to certain mucosa, such as genital and ocular sites. Also of particular interest with respect to vaginal delivery of naked polynucleotides are vaginal sandwich-type rings and pessaries. Examples of these devices and their use are described in Chien, supra at Ch.9.

The dosage of each naked polynucleotide or mixture thereof to be supplied using the method of the invention will vary depending on the desired response by the host and the polynucleotide used. Generally, it is expected that up to 100–200 μg of DNA can be administered in a single dosage, although as little as about 0.3 μg of DNA administered through skin or mucosa can induce long lasting immune responses.

For purposes of the invention, however, it is sufficient that the naked polynucleotides be supplied at a dosage sufficient to cause expression of the biologically active peptide encoded by the polynucleotide. Dosages suitable for particular indications (e.g., supplying a subtherapeutic dosage of cytokine) are illustrated by the discussion and examples provided below.

These dosages may be modified to achieve therapeutic, subtherapeutic or immunogenic levels of expression. Means to confirm the presence and quantity of expressed peptides are well-known to those skilled in the art and will not, therefore, be described in detail. Certain such means are illustrated in the Examples provided below; generally, they include immunoassays (such as enzyme-linked immunosorbent assays), PCR techniques, and immunohistological analyses performed according to techniques which are well known in the art. Dosages of the administered polynucleotides can be adjusted to achieve the desired level of expression based on information provided by these detection and quantification means as well as in vivo clinical signs known to practitioners skilled in the clinical arts.

II. ADMINISTRATION OF NAKED POLYNUCLEOTIDE COCKTAILS

Another aspect of the invention is the administration of a peptide cocktail (i.e., mixture of polynucleotides) via expression of gene constructs containing, for example, up to 200 polynucleotide sequences under the control of a single promoter. This embodiment will be of particular use in treating infections by agents of different species which cause similar symptoms. For example, there are over 100 known species of rhinoviruses which cause respiratory illnesses having similar clinical symptoms. Rather than undertaking the identification of the particular infecting species (a laborious and often inexact process), a cocktail vaccine could be administered according to the method of the invention which is capable of stimulating an immune response to many different rhinoviruses. This approach also allows for the construction of a vaccine to various strains of HIV, using pooled isolates of envelope genes from different patients (which genes may, if necessary, then be amplified).

Administration of mixtures of polynucleotides could also serve to deliver peptides having more than one biological activity. For example, a naked polynucleotide operatively encoding for an immunogenic peptide may be coupled to or administered with a naked polynucleotide operatively encoding an antibody in such a way that both peptide and antibody will be expressed. To illustrate, administration of genes which will jointly express IL-2 and anti-gp71 may (based on results obtained with the IL-2 protein) result in localization of the antibody in tumor tissue developed in response to murine leukemia virus (MuLV) in mice (see, re results obtained with concurrent administration of IL-2 /anti-gp71 mAb's, Schultz, et al., *Cancer Res.*, 50:5421–5425, 1990).

III. INDUCTION OF TUMOR-ASSOCIATED ANTIGEN-SPECIFIC CYTOTOXIC T LYMPHOCYTES

A. Production of Recombinant Immunoreactive Tumor-associated Antigen Mimics

This embodiment of the invention is based on the principle that peptides encoded by naked polynucleotides administered to tissues having a relatively high concentration of APCs according to the invention will be expressed intracellularly in the APCs (which then migrate into lymphatic tissue and stimulate an immune response). Thus, the method of the invention is particularly well suited to achieve intracellular expression of immunoreactive target antigens that will stimulate the development of antigen-specific class I restricted CTLs useful in cancer immunotherapy.

(1) Selection or identification of a tumor-associated antigen of interest and polynucleotide which encodes the antigen.

Although the method of the invention could be applied to generate CTLs against tumor-associated antigens on cells of an intact tumor, the method can be expected to have greatest efficacy when applied toward inducing CTL activity against residual cancer cells after removal of the primary tumor or organ associated with the tumor (where the latter is not required for life, such as endocrine and exocrine glands, sex organs, regions of the gastrointestinal tract and skin).

To that end, organ-specific or carcino-embryonic, tumor-associated antigen encoding polynucleotides will be selected or, if not known, identified. Examples of organ-specific, tumor-associated antigens whose cDNA coding sequences are known to those of ordinary skill in the art include the prostate-specific, transmembrane protein (PSM) (see, Israeli, et al., *Cancer Res.*, 54:1807–1811, 1994 and 53:227–230, 1993); breast eptithelial antigens (see, Ceriani, et al., *Anal. Biochem.*, 201:178–184, 1992); human gastrointestinal tumor antigen, Schistosoma mansoni-associated antigen, and melanoma specific antigen (see, Bellacosa, et al., *Mol. Cell Biol.*, 11:2864–2874, 1991). Carcino-embryonic antigen (which is localized to epithelia of the intestinal lumen; see, Benchimol, et al., *Cell*, 57:327–324, 1989) and the antigen associated with Wilm's tumor (which is localized in kidney; see, Roth, et al., *Verh. Dtsch. Ges. Pathol.*, 73:372–387, 1989), are examples of carcino-embryonic tumor associated antigens for which cDNA coding sequences are known and are suitable for use in the method of the invention.

Means for identification of additional tumor-associated antigens using well-known hybridization and/or polymerase chain reaction (PCR) techniques are described in Section I(A), supra. One method for identification of antigen-encoding polynucleotides which may be of particular use in identifying tumor-associated antigens for use in the invention is subtractive hybridization, which has recently been applied as a tool to identify genes which are present in one population, but not another, such as polymorphisms between the genome or particular genes of two individuals (see, Lisitsyn, et al., *Science*, 259:946–951, 1993, the disclosure of which is incorporated herein to illustrate knowledge in the art concerning the performance and use of cDNA subtractive hybridization techniques). Lisityn, et al. report that their subtractive hybridization method achieves better results than conventional subtractive hybridization techniques through the use of "kinetic enrichment"; i.e., through the use of PCR to melt and reanneal only a double-stranded "tester" DNA fragment present in lesser quantities than target DNA strands in a population of DNA fragments. The method is described as enabling "the discovery of genomic alterations occurring in cancer cells" (id. at 949).

Another method suitable for identification and isolation of genes uses the PCR to identify differentially expressed mRNAs is described in Liang and Pardee, *Science*, 257:967–971, 1992. This method uses a set of oligonucleotide primers, one being anchored to the polyadenylate tail of a subset of mRNAs, the other being short and arbitrary in sequence so that it anneals at different positions relative to the first primer. The mRNA subpopulations defined by these primer pairs are amplified after reverse transcription and resolved on a DNA sequencing gel. Using multiple primer sets, the authors report that they were able to obtain reproducible patterns of amplified complementary DNA fragments that showed strong dependence on sequence specificity in either primer of a primer pair.

For a review regarding the construction of cDNA libraries to isolate clones corresponding to mRNAs present in one cell or tissue type, but not another, those of skill in the art may wish to consult the standard protocols described in Ausubel, et al., *"Current Protocols in Molecular Biology"*, *Unit* 5.8B, Wiley & Sons, 1994, the disclosure of which is also incorporated herein by this reference to illustrate knowledge in the art concerning the construction of subtracted cDNA libraries). A brief review of suitable detection techniques utilizing the PCR is provided below.

In general, detection of targeted polynucleotides in samples or libraries by PCR involves the use of primers which embrace oligonucleotides of sufficient length and appropriate sequence to provide specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest. Specifically, the term "primer" as used herein refers to a sequence comprising two or more deoxyribonucleotides or ribonucleotides, preferably at least eight, which sequence is capable of initiating synthesis of a primer extension product that is substantially complementary to a target nucleic acid strand. The oligonucleotide primer typically contains 15–22 or more nucleotides, although it may contain fewer nucleotides as long as the primer is of sufficient specificity to allow essentially only the amplification of the specifically desired target nucleotide sequence (i.e., the primer is substantially complementary).

Experimental conditions conducive to primer synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition.

Primers used for PCR detection of tumor-associated antigens will be designed to be "substantially" complementary to each strand of nucleotide sequence to be amplified. Substantially complementary means that the primers must be sufficiently complementary to hybridize with their respective strands under conditions which allow the agent for polymerization to function. In other words, the primers should have sufficient complementarily with the flanking sequences to hybridize therewith and permit amplification of the mutant nucleotide sequence. Preferably, the 3' terminus of the primer that is extended has perfectly base paired complementarity with the complementary flanking strand.

Oligonucleotide primers are employed in any amplification process that produces increased quantities of target nucleic acid. Typically, one primer is complementary to the negative (−) strand of the mutant nucleotide sequence and the other is complementary to the positive (+) strand. Annealing the primers to denatured nucleic acid followed by extension with an enzyme, such as the large fragment of DNA Polymerase I (Klenow) or Taq DNA polymerase and nucleotides or ligases, results in newly synthesized +and -strands containing the target nucleic acid. Because these newly synthesized nucleic acids are also templates, repeated cycles of denaturing, primer annealing, and extension results in exponential production of the region (i.e., the target mutant nucleotide sequence) defined by the primer. The product of the amplification reaction is a discrete nucleic acid duplex with termini corresponding to the ends of the specific primers employed. Those of skill in the art will know of other amplification methodologies which can also be utilized to increase the copy number of target nucleic acid.

The oligonucleotide primers for use in the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters*, 22,:1859–1862, 1981). One method for synthesizing oligonucleotides on a modified solid support is described in U.S. Pat. No. 4,458,066. One method of amplification which can be used according to this invention is the polymerase chain reaction (PCR) described in U.S. Pat. Nos. 4,683,202 and 4,683,195.

The nucleic acid from any histologic tissue specimen, in purified or nonpurified form, can be utilized as the starting nucleic acid or acids, provided it contains, or is suspected of containing, the specific nucleic acid sequence containing the target nucleic acid. Thus, the process may employ, for example, DNA or RNA, including messenger RNA (mRNA), wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The nucleotide sequence to be amplified may be a fraction of a larger molecule or can be present initially as a discrete molecule, such that the specific sequence constitutes the entire nucleic acid. It is not necessary that the sequence to be amplified be present initially in a pure form; it may be a minor fraction of a complex mixture, such as contained in whole human DNA.

Where the target nucleotide sequence of the sample contains two strands, it is necessary to separate the strands of the nucleic acid before it can be used as the template. Strand separation can be effected either as a separate step or simultaneously with the synthesis of the primer extension products. This strand separation can be accomplished using various suitable denaturing conditions, including physical, chemical, or enzymatic means; the word "denaturing" includes all such means. One physical method of separating nucleic acid strands involves heating the nucleic acid until it is denatured. Typical heat denaturation may involve temperatures ranging from about 80° to 105° C. for times ranging from about 1 to 10 minutes. Strand separation may also be induced by an enzyme from the class of enzymes known as helicases or by the enzyme RecA, which has helicase activity, and in the presence of riboATP which is known to denature DNA. The reaction conditions suitable for strand separation of nucleic acids with helicases are described by Kuhn Hoffmann-Berling (CSH-*Quantitative Biology*, 43:63, 1978) and techniques for using RecA are reviewed in C. Radding (*Ann. Rev. Genetics*, 16:405–437, 1982).

If the nucleic acid containing the target nucleic acid to be amplified is single stranded, its complement is synthesized by adding one or two oligonucleotide primers. If a single primer is utilized, a primer extension product is synthesized in the presence of primer, an agent for polymerization, and the four nucleoside triphosphates described below. The product will be complementary to the single-stranded nucleic acid and will hybridize with a single-stranded nucleic acid to form a duplex of unequal length strands that may then be separated into single strands to produce two single separated complementary strands. Alternatively, two primers may be added to the single-stranded nucleic acid and the reaction carried out as described.

When complementary strands of nucleic acid or acids are separated, regardless of whether the nucleic acid was originally double or single stranded, the separated strands are ready to be used as a template for the synthesis of additional nucleic acid strands. This synthesis is performed under conditions allowing hybridization of primers to templates. Generally synthesis occurs in a buffered aqueous solution, preferably at a pH of 7–9, most preferably about 8. Preferably, a molar excess (for genomic nucleic acid, usually about $10^8$:1 primer:template) of the two oligonucleotide primers is added to the buffer containing the separated template strands. It is understood, however, that the amount of complementary strand may not be known if the process of the invention is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

In some amplification embodiments, the substrates, for example, the deoxyribonucleotide triphosphates dATP, dCTP, dGTP, and dTTP, are added to the synthesis mixture, either separately or together with the primers, in adequate amounts and the resulting solution is heated to about 90°–100° C. from about 1 to 10 minutes, preferably from 1 to 4 minutes. After this heating period, the solution is allowed to cool to room temperature, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C.

The agent for polymerization may be any compound or system which will function to accomplish the synthesis of primer extension products, including enzymes. Suitable enzymes for this purpose include, for example, *E. coli* DNA polymerase I, Taq polymerase, Klenow fragment of *E. coli* DNA polymerase I, T4 DNA polymerase, other available DNA polymerases, polymerase muteins, reverse transcriptase, ligase, and other enzymes, including heat-stable enzymes (i.e., those enzymes which perform primer extension after being subjected to temperatures sufficiency elevated to cause denaturation). Suitable enzymes will facilitate combination of the nucleotides in the proper manner to form the primer extension products which are complementary to each mutant nucleotide strand. Generally, the synthesis will be initiated at the 3' end of each primer and proceed in the 5' direction along the template strand, until synthesis terminates, producing molecules of different lengths. There may be agents for polymerization, however, which initiate synthesis at the 5' end and proceed in the other direction, using the same process as described above.

The newly synthesized mutant nucleotide strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules.

The above process is repeated on the single-stranded molecules. Additional agent for polymerization, nucleosides, and primers may be added, if necessary, for the reaction to proceed under the conditions prescribed above. Again, the synthesis will be initiated at one end of each of the oligonucleotide primers and will proceed along the single strands of the template to produce additional nucleic acid. After this step, half of the extension product will consist of the specific nucleic acid sequence bounded by the two primers.

The steps of denaturing and extension product synthesis can be repeated as often as needed to amplify the target mutant nucleotide sequence to the extent necessary for detection. The amount of the mutant nucleotide sequence produced will accumulate in an exponential fashion.

The amplified product may be detected by Southern blot analysis, without using radioactive probes. In such a process, for example, a small sample of DNA containing a very low level of target nucleotide sequence is amplified, and analyzed via a Southern blotting technique. The use of non-radioactive probes or labels is facilitated by the high level of the amplified signal.

Polynucleotides detected as described above can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed and are well known in the art (Landegren, et al., *Science*, 242:229–237, 1988).

(2) Where the antigen is a self-antigen (as opposed to a tumor-associated antigen from another mammalian species), modification of a polynucleotide which encodes the tumor-associated antigen of interest as a self-antigen to mimic, but not be identical to, the self-antigen.

To render a recombinant self-antigen "foreign" for purposes of avoiding immune tolerance to the self-antigen, it is generally sufficient to modify a single nucleotide in the coding region of the gene which codes for the self-antigen. The invention therefore provides a method for identifying which mutations in a tumor-associated antigen-encoding polynucleotide will be effective in modifying a self-tumor-associated antigen to an extent sufficient to break T lymphocyte tolerance thereto in a host (i.e., mutations which will produce immunoreactive "mimic" antigens for stimulation of specific autoimmune T lymphocyte responses).

To identify suitable mimic antigens for use in the invention, tumor-associated self-antigen-encoding polynucleotides will be mutated as described below. Preferably, the mutation will be made in the region of the polynucleotide which codes for an immunogeneic region of the self-antigen; i.e., for T cell epitope(s) in the self-antigen.

Although more laborious means of mapping T cell epitopes are known in the art, conveniently, epitopic regions of a protein can be predicted using Berzofsky's algorithm (see, Margalit, et al., *J. Immunol.*, 138:2213–2229, 1987, the disclosure of which is incorporated by this reference to illustrate knowledge in the art concerning the use of Berzofsky's algorithm). The algorithm screens overlapping amino acid residues in a protein and predicts the presence and location of T cell epitope(s) based on the ability of sets of residues to form an amphiphatic alphahelix configuration. The higher the amphiphatic score for a predicted epitope, the greater its probable immunoreactivity. A software program for applying the algorithm to amino acid sequences in a protein is commercially available under the tradename AMPHI program and is commonly used in the art to predict T cell epitopes. Rotzschike and co-workers have also recently described a method which they characterize as permitting "exact" prediction of a T cell epitope (Rotzschike, et al., *Eur. J. Immunol.*, 21:2431, 1991). Once T cell epitopes in a tumor-associated antigen are identified, isolated or sequenced and synthesized peptides containing the putative T cell epitope can be tested in a T cell proliferation assay to confirm the presence and reactivity of the epitope in the peptide.

Once epitopes in a tumor-associated self-antigen are identified, mutated polynucleotides which operatively encode mimic antigens can be produced, tested and/or administered according to the methods of the invention for use in cancer immunotherapy. Examples of suitable mutations include generation of a restriction fragment length polymorphism (RFLP), a nucleotide deletion, a nucleotide substitution, or any other mammalian nucleic acid sequence of interest. Therefore, as used herein the term "mutant or mutated" as applied to a polynucleotide sequence shall be understood to encompass a mutation, a restriction fragment length polymorphism, a nucleic acid deletion, or a nucleic acid substitution which render a tumor-associated antigen immunoreactive in the host. Particularly preferred mutations will be those which render a self-antigen similar in primary structure to a cross-reactive antigen from a different mammalian species (e.g., mouse and human ribonucleoproteins; see, e.g., Mamula, et al., *J. Immunol.,* 152:1453–1461, 1994). For purposes of this disclosure, immunoreactive mimic tumor-associated antigens produced by modification of self-antigens will be referred to as "homogenous tumor-associated antigen mimics", while tumor-associated antigens from a species other than the host species (which are immunologically similar to the tumor-associated antigens present on tumor cells in the host species) will be referred to as "hetereogenous tumor-associated antigen mimics".

Methods for mutation of polynucleotides to generate modified gene products are extant and well-known in the art. For example, a tumor-associated antigen-encoding polynucleotide having a desirable mutation may be produced by site-specific mutagenesis using a conventional polymerase chain reaction (PCR) and a primer pair corresponding to the 3' and 5' regions of the cDNA. A preferred method of mutation-generating PCR amplification is the overlap extension PCR technique described by Ho, et al., *Gene* 77:51–59 (1989), the disclosure of which is incorporated herein by this reference. Generally, this technique accomplishes site-specific mutagenesis of the clone by utilizing a 3' primer to add the mismatched mutating bases (primer B in the Ho article, which is used with the 5' primer A in the first PCR cycle described). Amplification using the A and B primers yields an AB fragment. A second PCR cycle uses a primer (D) from the 3' end of the gene and a 5' mutated primer (C) complementary to primer B. The resulting amplification product (fragment CD) will overlap the AB fragment. When the AB and CD fragments are denatured, reannealed and amplified using the A and D primers, the resulting fusion product (AD) will contain the full-length cDNA sequence and the desired mutation.

For generation of random mutations in genes, a PCR method modified to decrease the fidelity of Taq polymerase during DNA synthesis is particularly useful. Specifically, the PCR is performed under conditions that will generally produce a cumulative error frequency of 2% over the entire DNA nucleotide sequence and a mutant yield (for targets over 300 bp) of greater than 90%; to wit, conditions of high and pool-biased dNTP concentrations (1 mM each dTTP, dCTP, dGTP, 200 μM dATP), a high concentration of $MgCl_2$ in the presence of $Mncl_2$ (0.5 mM), and 25 PCR cycles starting with 1 ng cloned plasmid target. For a further review of this protocol for randomized PCR mutagenesis, those of skill in the art may wish to consult Leung, et al., *Technique,* 1:11–15, 1989; also, for a modification of the method to achieve random point mutations, Cadwell and Joyce, *PCR Methods and Applications,* 2:28–33, 1992; and, for generation of a PCR-derived library of random point mutations, Kirchoff and Desrosiers, *PCR Methods and Applications,* 2:301–304, 1993, the disclosures of which are incorporated herein by this reference to illustrate PCR mutagenesis methods known in the art.

Another suitable approach to making single base substitutions or deletions is described by Shaw in U.S. Pat. No. 4,904,584 ("Site-Specific Homogenous Modification of Polypeptides"), the disclosure of which is incorporated herein by this reference for purposes of illustrating knowledge in the art regarding methods for achieving specific mutations in a nucleic acid sequence.

(3) Rendering the naked tumor-associated antigen gene operatively encoding; i.e., by insertion into a recombinant expression vector.

Suitable techniques and vectors for use in this step of the invention are well-known to those of ordinary skill in the art or can be ascertained without undue experimentation; see, e.g., the review and discussion at Sections I(A) and II, supra.

B. Method for Screening of Therapeutically Effective Tumor-associated Antigen Mimics.

Once tumor-associated antigen mimics have been (a) identified according to step 1 above; and, (b) produced by expression using the polynucleotides and recombinant expression vectors constructed according to steps 2 and 3 above; or, (b') synthesized using conventional peptide synthesis methods, the mimics will preferably be screened for their ability to stimulate autoimmunoreactive CTLs which will lyse tumor cells which have the target tumor-antigen on the cell surface.

As discussed previously, CTL lysis of target cells depends on presentation of "foreign" peptides bound to class I MHC molecules. Thus, tumor-associated antigen mimics suitable for use in cancer immunotherapy will be those which will form peptide/MHC complexes on the surface of APCs in vivo. Peptides bound to class I MHC molecules on APCs are believed to be characterized by having a length of about 8 to 10 amino acid residues (see, e.g., Falk, et al., *Nature,* 351:290, 1991; and, Jardetzky, et al., *Nature,* 353:326, 1991). It has been shown that when such peptides are recombinantly expressed in transfected APCs, they can bind class I MHC (see, e.g., Townsend, et al., *Cell,* 42:457, 1985; Townsend, et al., *Nature,* 324:575, 1986; and, Shastri, et al., *J. Immunol.,* 150:2724–2736, 1993).

The invention provides a method for determining whether a candidate tumor-associated antigen-encoding polynucleotide has "therapeutic efficacy"; i.e., will express a tumor-associated antigen mimic in the cytoplasm of APCs, which antigen will in turn (a) become bound to class I MHC molecules on the APC cell surface; and (b) stimulate CTL lysis of host tumor cells bearing the target tumor-associated antigen.

To determine if a candidate tumor-associated antigen mimic recombinantly expressed in APCs will become bound to class I MHC, conventional techniques such as mass spectrometric analysis of transfected APCs may be used. However, another technique which is preferred for its convenience involves transfection of MHC expressing CHO (chinese hamster ovary) cells as model APC with a candidate tumor-associated antigen mimic encoding polynucleotide. Once expression of the mimic in transfected APCs is confirmed (by, for example, Western blotting), binding of the expressed mimic to class I MHC molecules may be confirmed in an in vitro antigen-specific T cell activity assay.

Protocols for such assays are well-known and will not, therefore, be described in detail here. However, for review, those of skill in the art may wish to consult Coligan, et al., "*Current Protocols in Immunology*", Unit 3.11, Wiley & Sons, 1994 (in particular, Unit 3.11.2, the basic protocol for assaying T cell lytic activity in response to stimulation by MHC antigens). For a source of responder cells which are predictive of antigen processing and presentation mechanisms in human APCs, such mechanisms have been shown to be highly conserved between murine and simian species (see, e.g., Shastri, et al, supra at 2727–2728), such that mouse or non-human primate cells will be suitable models for use in T cell activity assays to predict tumor-associated antigen mimic presentation by human APCs.

Similarly, murine and non-human primate animal models will be suitable for predicting in vivo CTL responses to APCs transfected in vivo according to the method of the invention; i.e., whether such APCs can stimulate CTL responses against tumor-associated antigens on tumor cells in the host. Most conveniently, one model for determining antigen-specific CTL activity involves the use of recipient mice without endogenous active T lymphocytes; e.g., nude mice or irradiated mice. Adoptive transfer of tumor-associated antigen primed CTLs into mice in whom tumor cells from a host or cell line have been introduced allows for in vivo assessment of the lytic ability of the transferred CTLs vis-a-vis the tumor cells (see, e.g., the standard protocols for adoptive transfer, CTL depletion and in vivo T cell activity assays described in Coligan, et al., "*Current Protocols in Immunology*", supra at Unit 4.1; see also, Shastri, et al., supra at 2734 [based on estimates of processed peptides isolated from APCs and the number of peptide-bound MHC thereon extrapolated from Scatchard plots, the minimum number of peptide/MHC complexes required for T cell stimulation in vivo ranges between 100 and 1000 copies/cell]).

Using the above-described screening method, tumor-associated antigen mimic-encoding polynucleotides can be identified and constructed for use in cancer immunotherapy according to the in vivo administration method of the invention, or for generation of antibodies for uses such as affinity purification of tumor-associated antigens and mimics.

C. Method for Cancer Immunotherapy by Administration of Naked Polynucleotides that Operatively Encode Tumor-associated Antigens and Tumor-associated Antigen Mimics (1) Administration of the operatively encoding polynucleotide as a naked polynucleotide according to the invention.

Methods for administration of operatively encoding naked polynucleotides according to the invention are described in Section I(C), supra. The skin and mucosa will be particularly efficacious sites for administration of naked polynucleotides which encode the antigens of interest for treatment of a particular malignancy. These areas of the body are the sites where most viruses and other antigens that induce CTL responses first encounter the host. Fortuitously, these sites are also those outside of the lymphatic system which tend to contain the highest concentrations of APC's (e.g., approximately 1-2% of the cells in the epidermis are macrophages and dendritic cells).

The naked, tumor-associated antigen encoding polynucleotides of the invention will be administered according to medically accepted parameters for cancer immunotherapy; e.g., pertaining to course of treatment and containment of side effects. Preferably, the method of the invention will be used to stimulate a tumor-associated antigen-specific CTL response against residual tumor cells bearing the antigen after removal of the organ or tissue in which the tumor resided. Most preferably, the method of the invention will be used to stimulate a tumor-associated antigen-specific CTL response against tumor cells in tissues of the host having a relatively high concentration of APCs therein; e.g., skin or mucosa.

It has been reported in the art that T lymphocyte tolerance to self-antigens is more effectively broken through co-immunization of the host with self antigens and foreign antigens that resemble self-antigens (see, Mamula, et al., *J. Immunol.*, supra at 1456). Thus, to optimize the breakdown of T lymphocyte tolerance to the tumor-associated antigen in the host, the host will preferably be treated with both polynucleotides which encode homologous and heterologous tumor-associated antigens.

Optionally, the host will be co-immunized with protein tumor-associated antigen vaccines (according to medically accepted parameters for cancer immunotherapy) to stimulate assistance by helper T lymphocytes and/or with cytokine-encoding polynucleotides to enhance the performance of the host's immune system (see, e.g., Section I, supra and Caligiuri, et al., *J. Clin. Invest.*, 91:123-132, 1993, [infusions of recombinant IL-2 protein to patients with advanced cancers]).

However, because the development of anti-tumor associated antigen soluble antibodies will be accompanied by the release of soluble antigen (which poses the risk of interference with CTL activity and of encouraging immune complex disease), the preferred practice of the invention will induce CTLs without inducing antibody formation (by avoiding the extracellular release of soluble antigen as discussed above).

Figure 12:
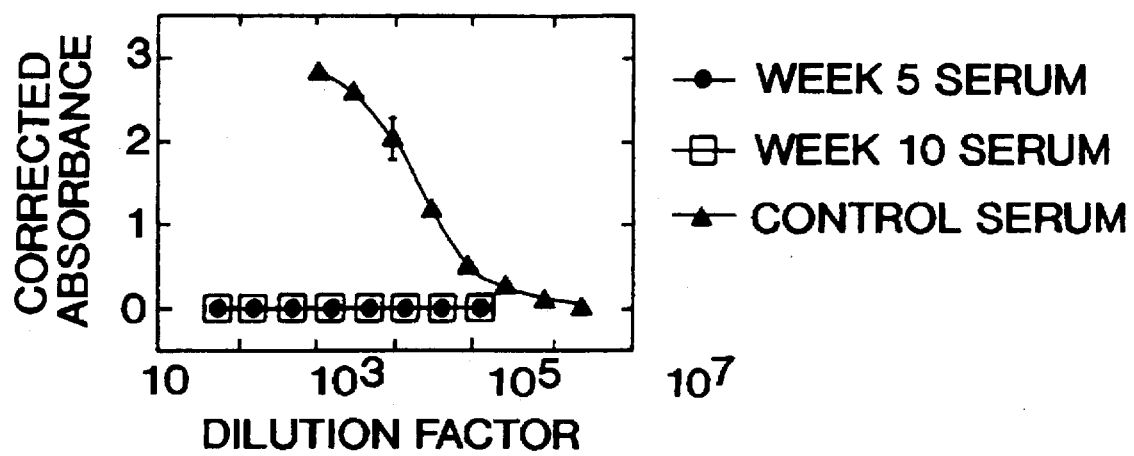
FIG. 12 depicts the results of an ELISA for anti-ovalbumin antibodies in sera from the mice described with respect to FIG. 12.

In Example IX, antigen-encoding polynucleotides were injected intradermally into mice for expression in APCs according to the invention. As shown in FIGS. 11 and 12, antigen-specific CTLs were detected in sera from the mice after injection, yet no antibodies reactive with the injected antigen were detected. In this respect, it should be noted that the inventors have demonstrated that adminstration of antigens according to the method of the invention selectively boosts production of TH1 lymphocytes in preference to TH2 lymphocytes (see, Examples XI and XII and co-pending U.S. patent application Ser. No. 08/333,068, filed Nov. 1, 1994.). Thus, the method of the invention will stimulate the tumor-associated antigen specific CTL response required for effective cancer immunotherapy without stimulating autoantibody production (i.e., against tumor associated self-antigens in the host).

Examples illustrating aspects of each embodiment of the invention are provided below. They should be regarded as illustrating rather than limiting the invention.

EXAMPLE I

LOCALISED DELAYED HYPERSENSITIVITY RESPONSES IN MICE OCCUR FOLLOWING INTRAMUSCULAR INJECTIONS OF NAKED POLYNUCELOTIDE

Although (consistent with previously reported results) intramuscular injection of naked plasmid cDNA results in expression of peptides encoded by the polynucleotides, it also (contrary to previously reported results) elicits an immune response to the gene in the muscle tissue. With co-injection of 2 plasmids, this inflammatory response becomes chronic, with myonecrosis being exhibited. Both responses are consistent with a diagnosis of a localized delayed hypersensitivity response to the gene at its point of entry, i.e., muscle tissue. Contrary to previous assumptions, it is this inflammatory response rather than uptake by muscle cells which is likely (if not solely) responsible for expression of naked polynucleotides following intramuscular injections thereof.

To illustrate the immune response caused by intramuscular injection of naked cDNA, pREVk3 and pRSVIL2 were prepared as follows.

Preparation of Plasmids. A rearranged kappa light gene from a human patient with chronic lymphocytic leukemia was isolated which contains a Humkv 325 (which encodes the 17.109 cross-reactive idiotype commonly expressed by IgM autoantibodies and chronic lymphocytic leukemia cells). This gene is known in the art and is described, for example, in Martin, et al *J. Exp. Med.*, 175:983, (1992), which article is incorporated herein by this reference.

A 1040 bp HindIII-XhoI fragment containing the V-J region of this gene was excised and inserted into the polycloning site of the mammalian expression vector pREP7 (Invitrogen, San Diego, Calif.), downstream of the Rous sarcoma virus (RSV) long terminal repeat (LTR) to produce a vector designated pREVk3. Downstream of the rearranged JK1 segment, there is a natural stop codon, which terminates translation.

To produce an IL-2 expression vector, designated pRSVIL-2 , the luciferase cDNA in the vector pRSVL (Wolff, et al., *Science*, 247:1465, 1990) was replaced with a 680 bp HindIII-BamHI fragment of pBC12/HIV/IL-2 (American Type Culture Collection, No. 67618) according to the method taught in Cullen, *Cell*, 46:937, (1986). The Wolff, et al., and Cullen references are incorporated herein to illustrate knowledge in the art concerning construction of these expression vectors.

Intramuscular injection of mice with plasmid cDNA. Eight week old BALB/c mice were anesthetized with methoxyflurane. Plasmid cDNA (100 μg per injection) was suspended in 100 μl of saline, and then was injected four times into the quadricep muscles through a 28-gauge needle at weekly intervals. One group of six mice received 100 μg of pREVk3. Another group of six mice received 100 μg each of pREVk3 and pRSVIL-2 while a third group received 100 μg of saline alone. Just before every injection, blood samples were collected from the orbital arteries.

ELISA To Verify In Vivo Gene Expression by the Plasmids. Antibodies against Humkv325 products were measured by ELISA (enzyme-linked immunosorbent assay). The IgM rheumatoid factor Glo is encoded by the Humkv325 gene and has 17.109 idiotype positive kappa light chains. The purified protein was dissolved at 10 μg/ml in 0.1M borate, 0.2M NaCl, pH 8.2 (i.e., buffered borate saline or BBS), and then 100 μl aliquots were added to the wells of plastic microtiter plates. After overnight incubation at 4° C., the plates were washed twice with BBS containing 0.5% Tween-20 (BBS/Tween), and were quenched with BBS supplemented with 1% bovine serum albumin (BBS/BSA) for four hours at room temperature. After washing twice with BBS/Tween, samples diluted serially in BBS/BSA were distributed to the wells in duplicate. After incubation for three hours at room temperature, the plates were washed four times with BBS/Tween, and then were incubated with biotinylated gout anti-mouse IgG (Kirkegaard & Perry, Gaithersburg, Md.) diluted to 1:2000 in BBS/BSA. One hour later, the plates were washed four times with BBS/Tween, and incubated with 25 μl of TMB peroxidase substrate (Kirkegaard & Perry). Thirty minutes later absorption at 450 nm was measured in a microplate reader (Molecular Devices, Menlo Park, Calif.). To estimate the antibody content in the immune sera, the results were compared to a standard curve made with monoclonal antibody 17.109 (see, e.g., the description of this mAb at Carson, et al., (1983) *Mol. Immunol.* 20:1081-1087).

These assays showed that production of the antibodies of interest had been enhanced, thereby confirming expression of the genes by the plasmids.

Histological evaluation. At day 49 the intramuscularly injected mice were sacrificed. Muscles into which the genes had been injected were fixed in 10% formalin and processed for histological evaluation.

Figure 1C:
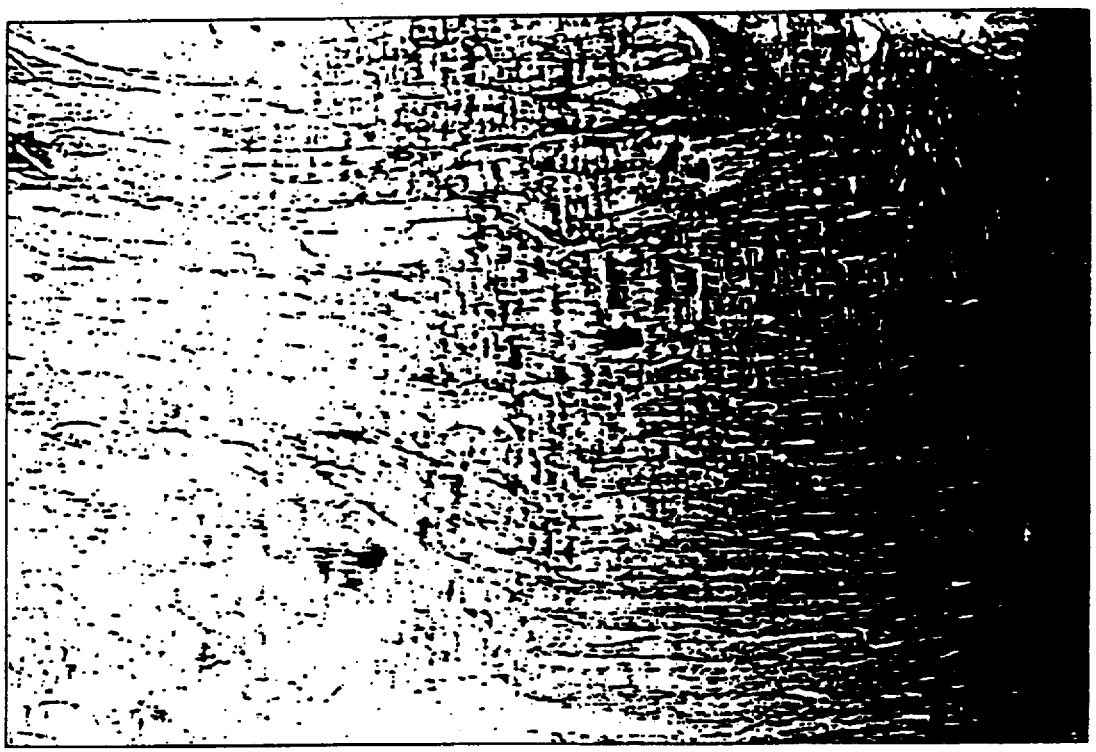
FIG. 1C depicts sections of similar muscle tissue following subcutaneous injections of pREVK3 or pRSVIL-2.

Sections from muscles that had been co-injected with pREVk3 and pRSVIL2, demonstrated chronic inflammation and myonecrosis, consistent with a localized delayed hypersensitivity response (FIG. 1A and B). In contrast, muscles injected with pREVk3 or pRSVIL2 alone had a lymphoid infiltrate localized to the site of subcutaneous injection (FIG. 1C).

EXAMPLE II

GENE EXPRESSION FOLLOWING INTRADERMAL INJECTION OF A NAKED POLYNUCLEOTIDE

To explore alternatives to intramuscular injections of naked polynucleotides, mice were injected with a naked cDNA plasmid intradermally. Gene expression was observed and measured.

The gene for influenza ribonucleoprotein (RNP) was subcloned into a pCMV plasmid as described above. RNP genes from numerous strains of influenza are known in the art and are highly conserved in sequence among various strains (see, e.g. Gorman, et al., *J. Virol*, 65:3704, 1991).

Four eight week old Balb/c mice were injected three times with 15 μg of pCMV-RNP suspended in 100 μl of HBSS. Injections were made intradermally at the base of the tails at two week intervals. Cytotoxic T lymphocytes (CTL) recognize antigens presented by class I MHC molecules and play an important role in the elimination of virally infected cells. Intramuscular (i.m.) immunization by means of cDNA expression vectors should be an effective method to introduce antigen into class I MHC molecules and thus stimulate CTL responses. In this study, intradermal (i.d.) injection of a plasmid containing the influenza nucleoprotein (NP) antigen gene induced both NP-specific CTL and high titers of anti-NP antibodies. These antibodies reached a maximum 6 weeks after injection and persisted unchanged for at least 28 weeks, in the absence of local inflammation.

Plasmid DNA was purified by CsCl banding in the presence of ethidium bromide and was stored frozen in 10 mM Tris-HCL, 0.1 mM EDTA, pH 8.0. Before injection, the plasmid was precipitated in ethanol and dissolved in normal saline containing 0.1 mM EDTA.

Figure 2A:
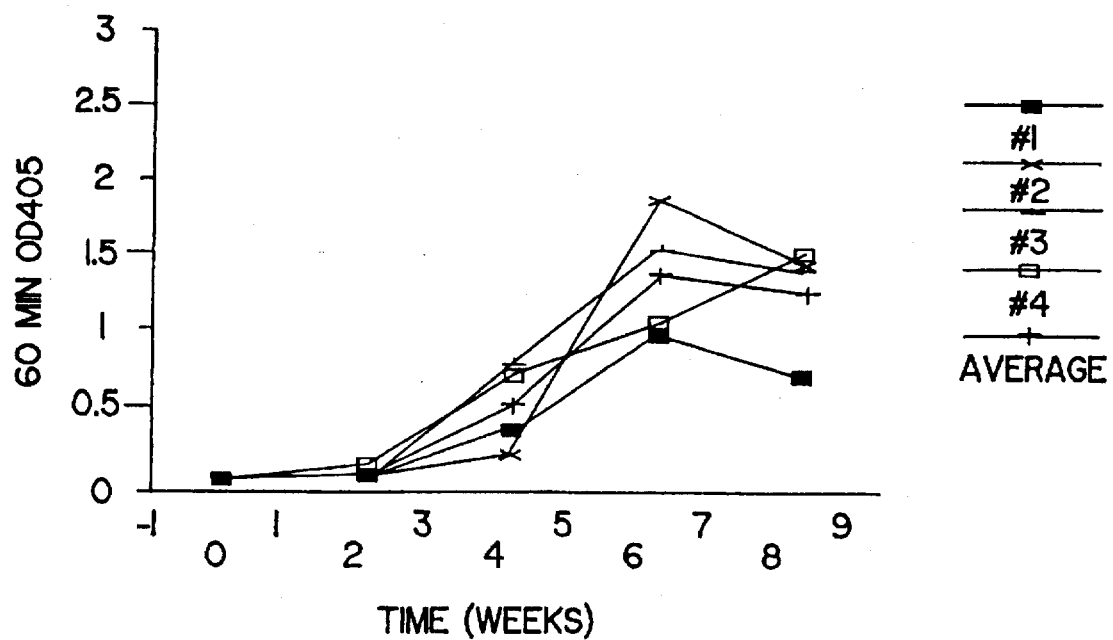
FIG. 2A depicts the results of an ELISA for anti-NP IgG in serum following intradermal injection of naked pCMVRNP.
Figure 2B:
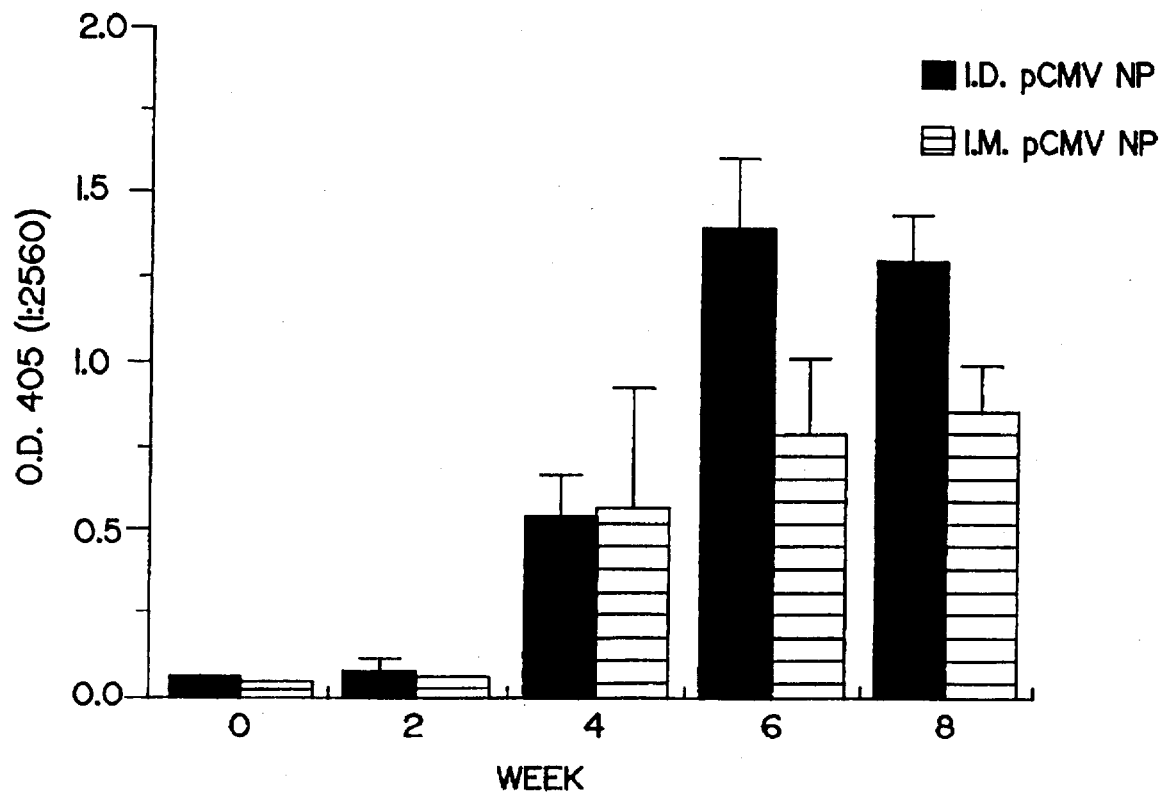
FIG. 2B depicts the results of an ELISA for anti-NP IgG in serum following intramuscular injection of naked pCMVRNP.

The presence of anti-NP IgG in serum was measured by ELISA substantially as described in Viera, et al., *Int. Immunl.*, 2:487, (1990). The results of this assay are shown in FIG. 2A; all of the animals developed high titer anti-NP antibodies, which persisted for more than 20 weeks. As shown in FIG. 2B, the intradermal injections appeared to give about four fold higher antibody titers than intramuscular injections (made as described in Example I) of equivalent amounts of plasmid DNA.

The axes of FIG. 2 represent, respectively, the ELISA titer (mean, 1 ounce) against time. Serum dilution for all graph points is 2560.

EXAMPLE III

GENE EXPRESSION FOLLOWING INTRANASAL INTRODUCTION OF A NAKED POLYNUCLEOTIDE

Using the same plasmid (pCMV-RNP) in the same HBSS suspension described in Example II, naked polynucleotide encoding for influenza ribonucleoprotein was introduced to Balb/c mice in 3 groups of 6 intranasally. Levels of anti-NP IgG in peripheral blood before and after introduction of the plasmid at various serum dilutions were measured by ELISA as described in Example II. Blood was drawn from each mouse after intranasal introduction after 6 weeks.

Figure 3:
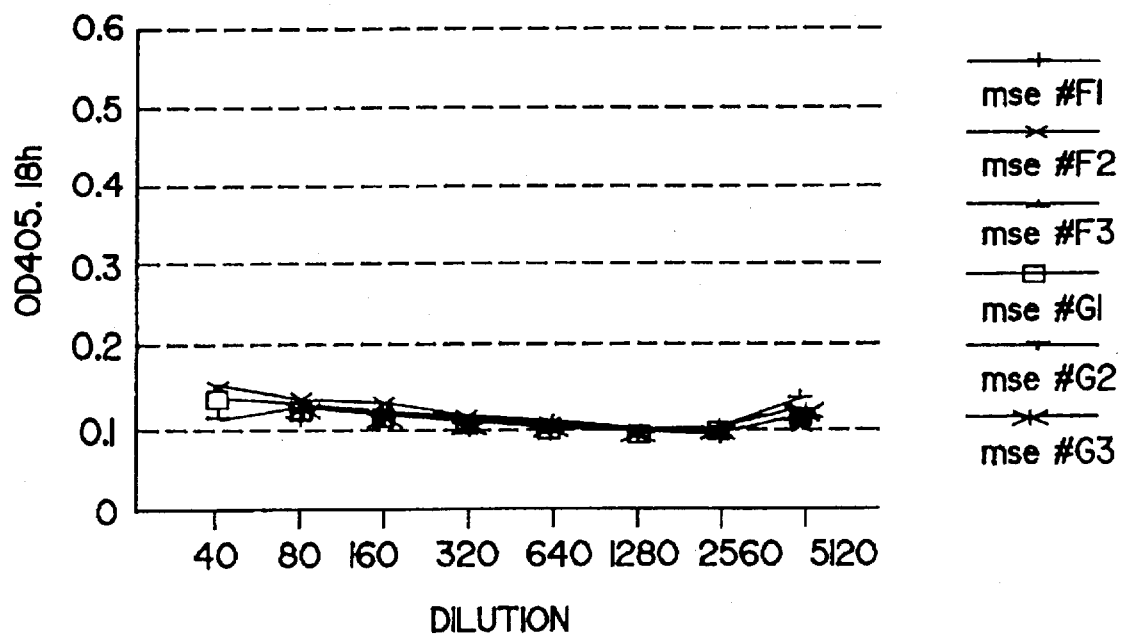
FIG. 3 depicts the results of an ELISA for anti-NP IgG before intranasal introduction of naked pCMVRNP to Balb/c mice.

FIG. 3 graphically depicts the results of the ELISA assays before and after intranasal introduction of the plasmid. The graphs plot ELISA titer against serum dilution. In FIG. 3, values are shown for individual mice from each group (#1-3) and an average value from all mice in each group (#G1-G3).

Figure 4:
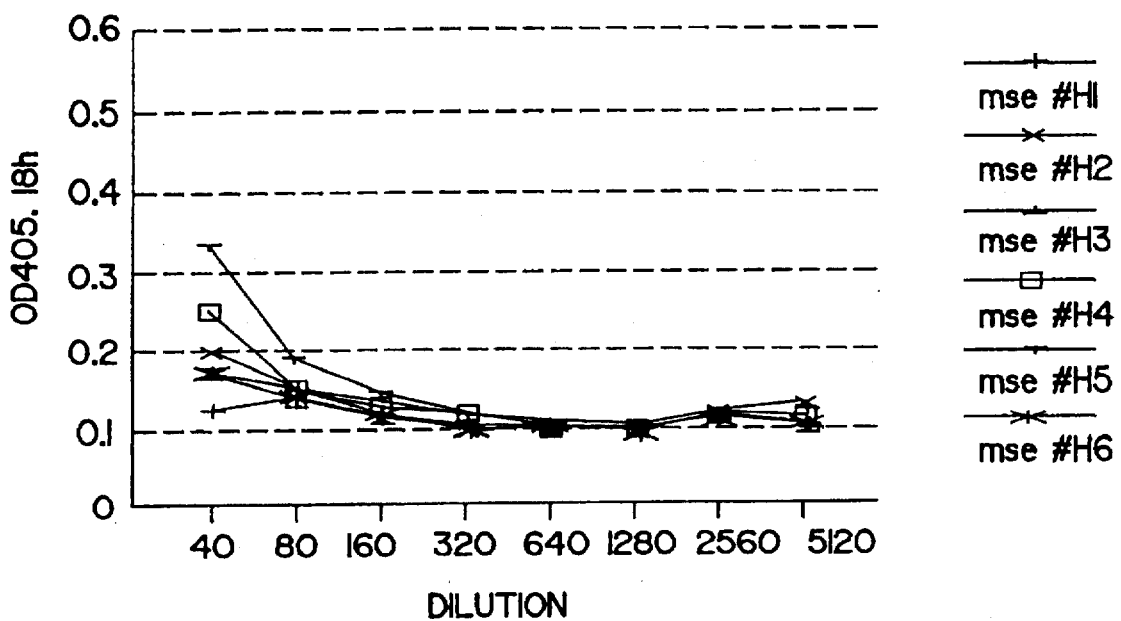
FIG. 4 depicts the results of an ELISA for anti-NP IgG in an unanesthesized group of Balb/c mice.

Without anesthesia, mice in a second group which received 3×7.5 µg of plasmid showed enhanced titers of antibody as compared to background (FIG. 3). These data are shown in FIG. 4.

Figure 5:
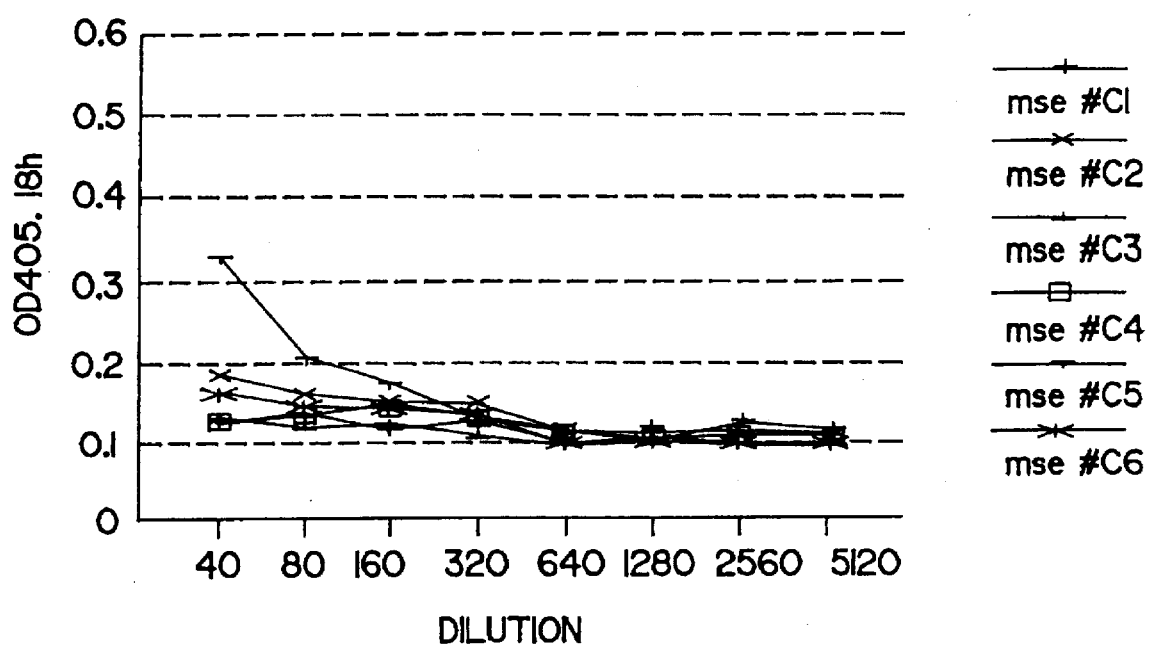
FIG. 5 depicts the results of an ELISA for anti-NP IgG in an anesthesized group of Balb/c mice.

A third group of mice received the same gravity of plasmid under anesthesia. Expression of RNP as indicated by titers of anti-NP IgG in these mice was substantially similar to the expression achieved in the unanethesized mice. The data for the anethesized mice are shown in FIG. 5.

Expression can be enhanced by additional use of absorption promoters, and prolonged by time-released promoters whose identity and use are known in the art such as those suggested in Chien, supra, at Ch. 5.

EXAMPLE IV

HISTOLOGICAL STUDIES SHOWING CELL UPTAKE OF NAKED POLYNUCLEOTIDES BY MONONUCLEAR CELLS AT THE POINT OF ENTRY IN SKIN

Three days after intradermal injection of the tails of naked pCMVlacz into Balb/c mice, the mice were sacrificed. Tissue cultures were obtained at the point of entry for the plasmid and stained for $E.\ coli$ β-galactosidase activity. A photograph (40× magnification) of a slide from the histological examination of these cultures is contained in FIG. 6.

Figure 6:
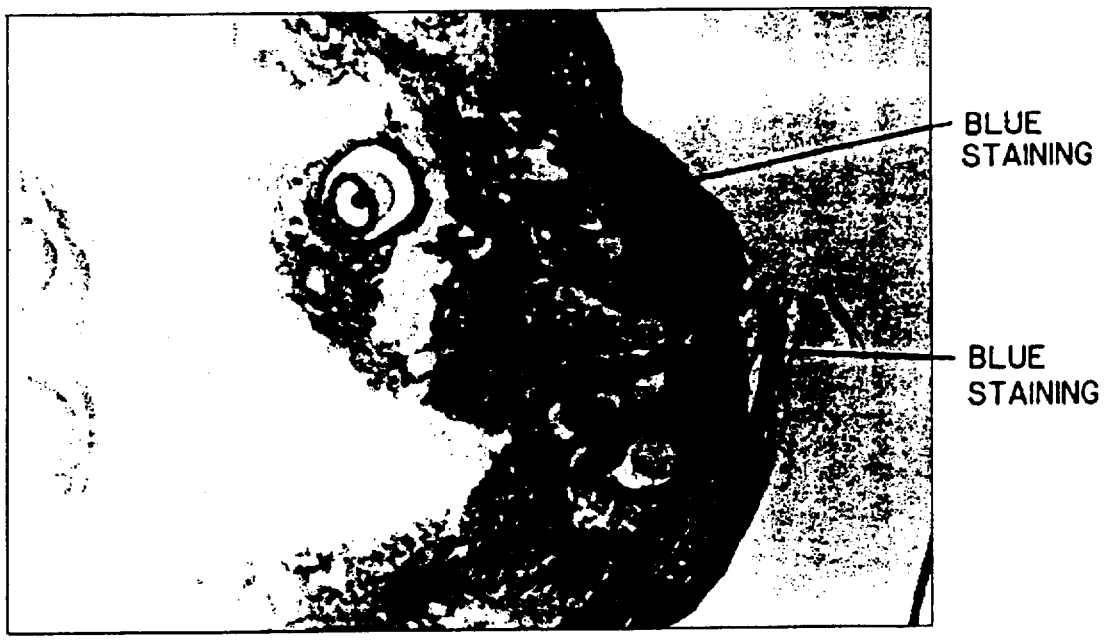
FIG. 6 is a photograph of the results of histological studies of skin at the point of entry for pCMVRNP in Balb/c mice showing uptake of the plasmid by mononuclear cells (APC's). An APC is indicated by an arrows; a tissue cell (not containing the plasmid) is indicated by a slashed line.

As shown in FIG. 6, uptake of the plasmid is shown (in blue) to be by mononuclear cells. The fibroblasts in the tissue samples are not stained, thus indicating that the plasmid was not taken up by these cells. The rounded, mononuclear cells which did take up the plasmid appear to be macrophages and/or other antigen presenting cells, which would indicate that uptake of the plasmid is by phagocytosis.

EXAMPLE V

EPIDERMAL ADMINISTRATION OF A NAKED POLYNUCLEOTIDE USING A MECHANICAL IRRITANT TO ELICIT AN IMMUNE RESPONSE

Figure 7:
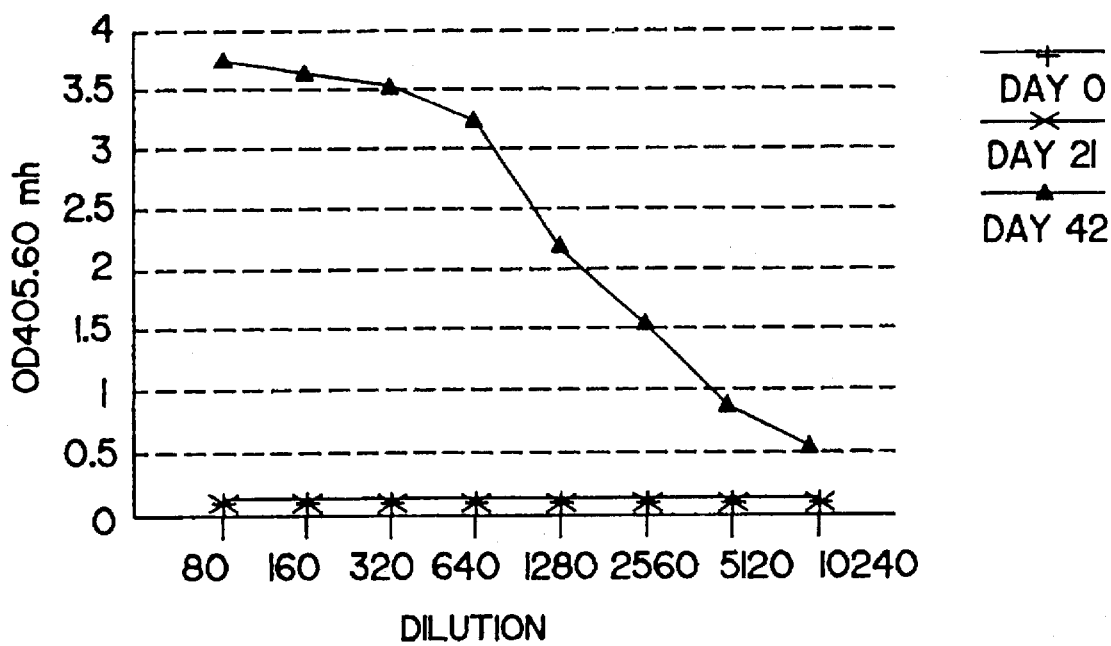
FIG. 7 depicts the results of an ELISA for anti-NP IgG following mechanical epidermal administration of naked pCMVRNP to Balb/c mice.

FIG. 7 depicts the results of an ELISA performed as described in Example I for serum levels of anti-NP IgG following epidermal administration of pCMVRNP via mechanical means.

The plasmid was coated onto the tynes of an uncoated MONO-VACC® device as described supra. (It should be noted that it is alternatively possible for the naked polynucleotides to be lyophilized onto the tynes of the device for longer storage stability). Total plasmid concentration on all of the device tynes was approximately 50 µg in an isotonic normal saline carrier (approximately 150 µg plasmid per milliliter). The back of a Balb/c mouse was shaved and the shaved skin gently scratched with the tyne device. As shown in FIG. 7, anti-NP IgG were subsequently detected in serum (e.g., at day 42, the serum from this mouse contained antibodies at a titer of 1:10240).

EXAMPLE VI

EPIDERMAL ADMINISTRATION OF A NAKED POLYNUCLEOTIDE USING A CHEMICAL AGENT TO ELICIT AN IMMUNE RESPONSE

Figure 8:
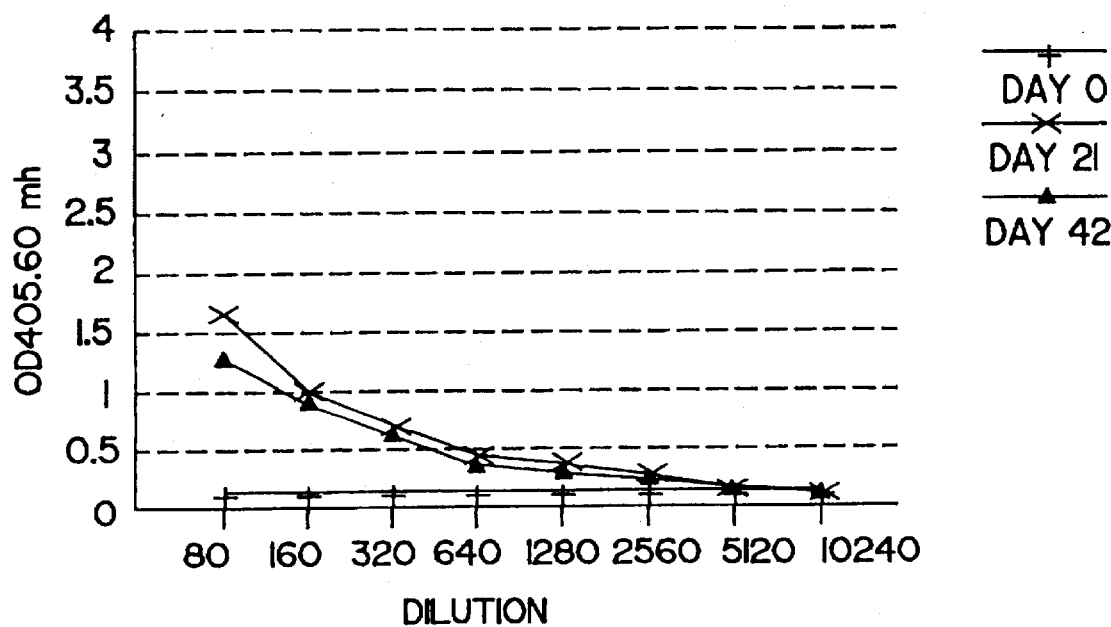
FIG. 8 depicts the results of an ELISA for anti-NP IgG following chemical epidermal administration of naked pCMVRNP to Balb/c mice.

FIG. 8 depicts the results of an ELISA performed as described in Example I for serum levels of anti-NP IgG following epidermal administration of pCMVRNP in conjunction with the application of a chemical agent.

The plasmid was suspended in 40 µg of an isotonic normal saline solution containing approximately 150 µg of plasmid per milliliter. This solution was absorbed onto the nonadhesive pad of a BAND-AID brand bandage (Johnson & Johnson).

A Balb/c mouse was shaved as described in Example V and a commercially available keratinolytic agent (here, the previously described depilatory creme sold under the tradename NAIR) was applied to the shaved skin. After several minutes, the keratinolytic agent was washed off of the skin and the plasmid-containing bandage applied thereto. As shown in FIG. 8, the treated animal developed serum anti-NP IgG at a titer of 1:640.

EXAMPLE VII

IMMUNE RESPONSE TO VIRAL CHALLENGE BY MICE INTRADERMALLY INJECTED WITH NAKED pDCMVRNP

To test whether immunity generated by vaccination with appropriate naked polynucleotides could protect animals from a lethal viral challenge, groups of 10 Balb/c mice were injected intradermally 3 times with 15 µg of a pCMVRNP plasmid which contained the NP gene from an H1N1 strain of influenza virus (A/PR/8/34; provided by Dr. Inocent N. Mbawvike at the Baylor College of Medicine, U.S.) Control groups included uninjected animals as well as animals injected with an irrelevant plasmid (pnBL3).

Figure 9:
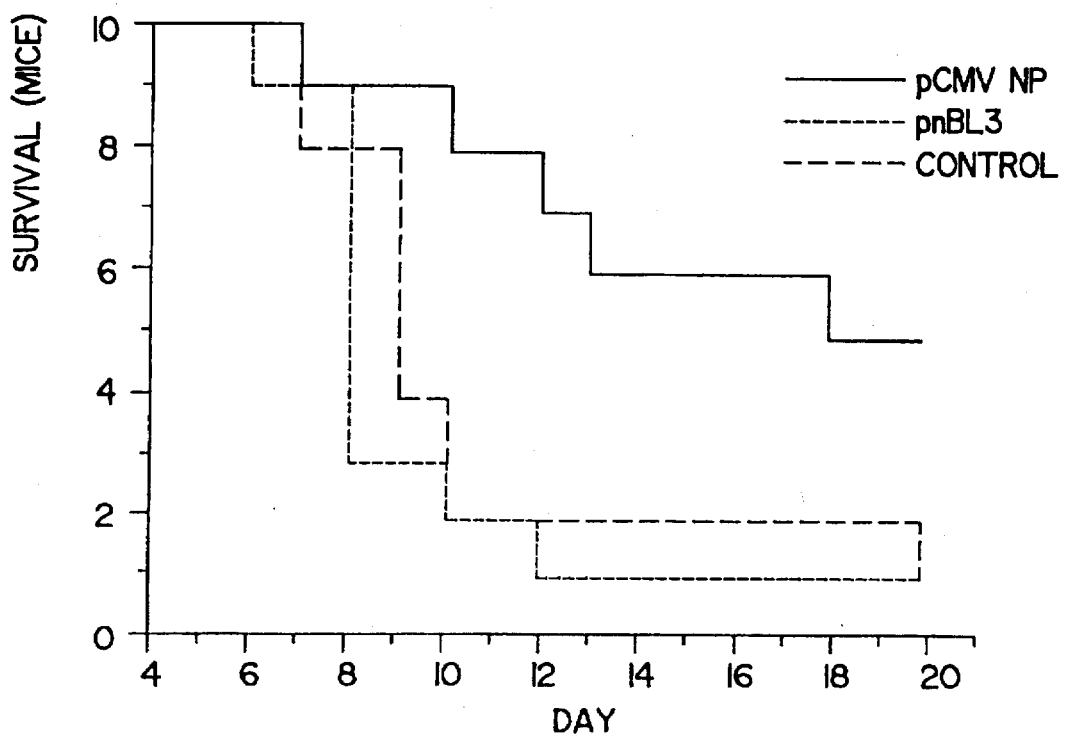
FIG. 9 contains a Kaplan-Meyer survival curve depicting the length of time that Balb/c mice injected intradermally with naked pCMVRNP survived following viral challenge.

Six weeks after the initial plasmid injections, the animals were challenged with a $LD_{90}$ dose of an H3N2 influenza strain (A/HK/68); also provided by Dr. Mbawuike). Intradermally vaccinated mice were significantly protected from the challenge (P(0.01) as compared to unvaccinated control mice; see, FIG. 9 (a Kaplan-Meyer survival curve).

EXAMPLE VIII

RELATIVE LEVELS OF GENE EXPRESSION FOLLOWING INTRADERMAL INJECTIONS OF NAKED CYTOMEGALOVIRUS OR ROUS SARCOMA VIRUS PROMOTER-CONTAINING NAKED PLASMIDS

Figure 10:
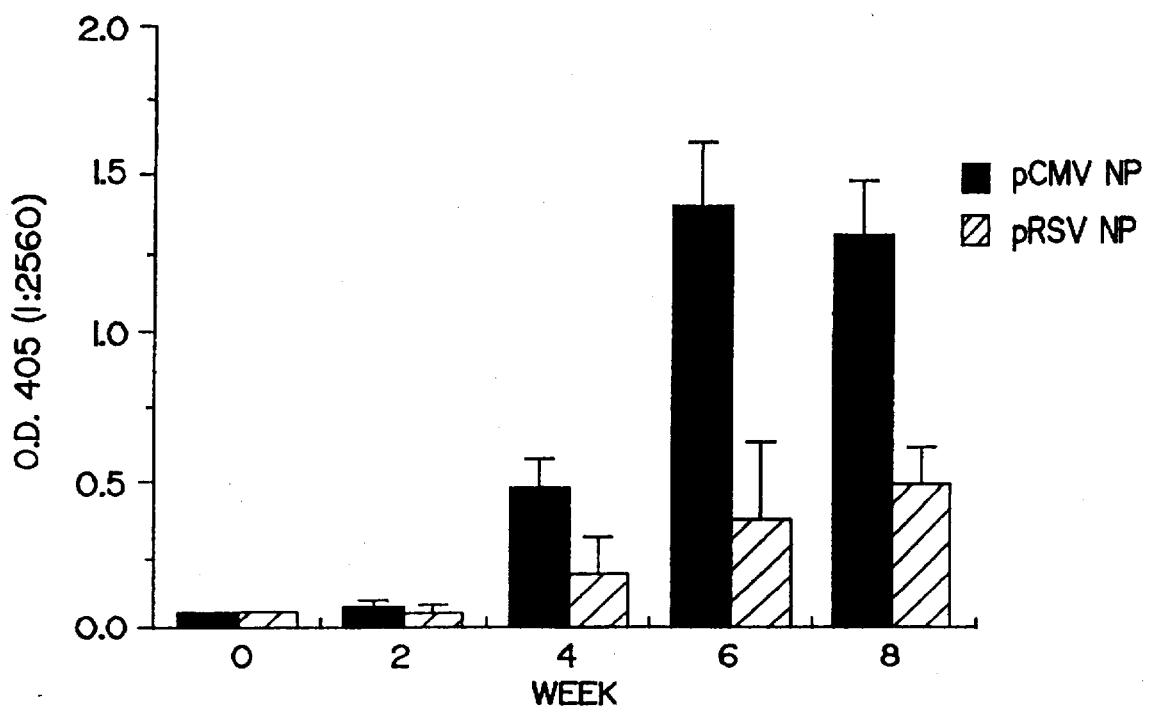
FIG. 10 graphically compares NP gene expression following separate intradermal injections of naked plasmids containing either a CMV or an RSV promoter sequence.
Figure 11B:
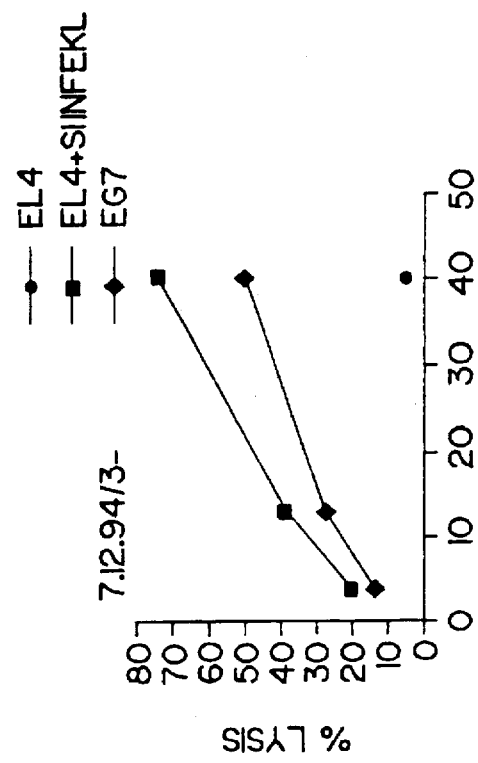
FIG. 11 depicts the levels of cytotoxic T cells detected in mice after injection of ovalbumin cDNA and ovalbumin administered by intradermal injection.
Figure 11D:
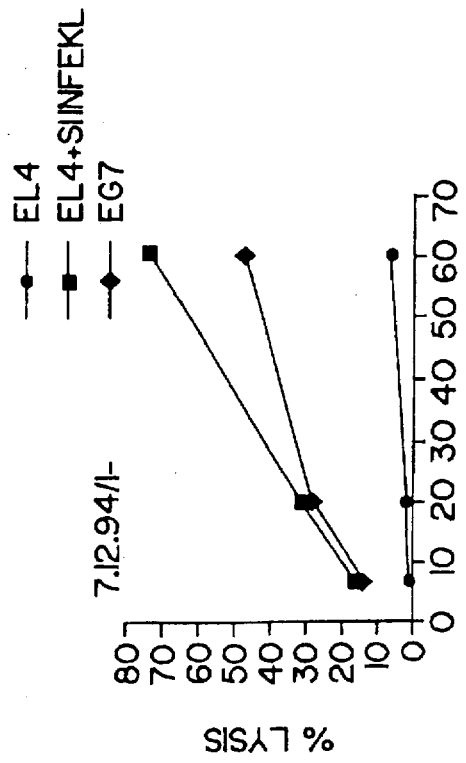
Figure 11A:
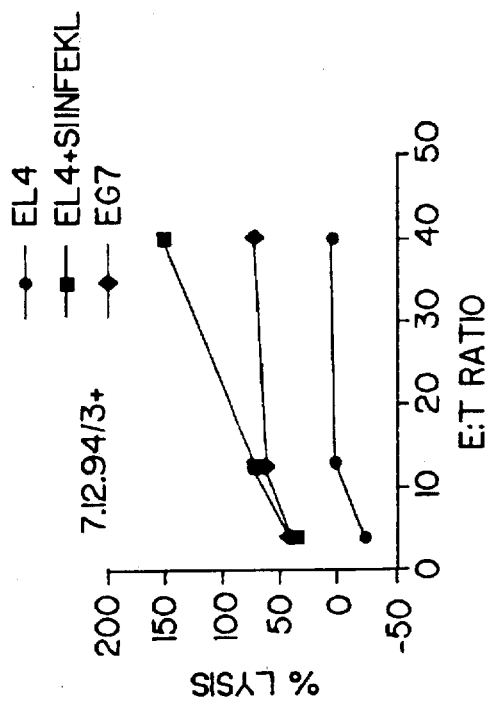
Figure 11C:
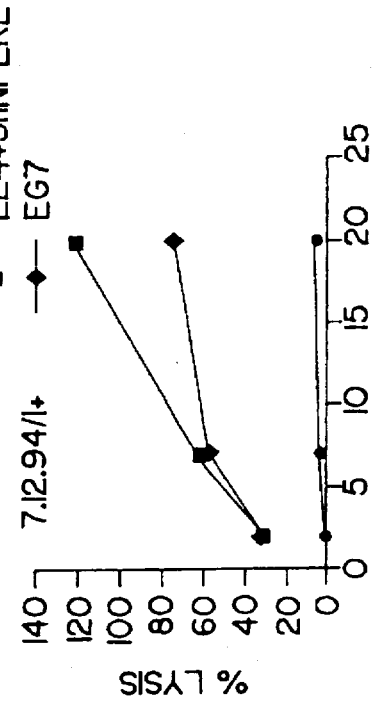

The possible effect of the promoter region used in an expression vector was evaluated by testing two plasmids which contain the RNP gene described in Example II. One plasmid, pCMVRNP, contained the cytomegalovirus immediate early promoter, enhancer and intron region. The other plasmid contained the promoter from the Rous sarcoma virus LTR region (pRSVRNP). As shown in FIG. 10, antibody responses to the NP protein expressed by the plasmids were consistently higher with the CMV promoter after intradermal injections. This contrast with the responses seen after intramuscular injection of the NP gene, where antibody levels produced by the two plasmids are essentially equivalent (data not shown).

EXAMPLE IX

SELECTIVE INDUCTION OF CYTOTOXIC T LYMPHOCYTE RESPONSES AFTER INTRADERMAL ADMINISTRATION OF NAKED POLYNUCLEOTIDES

Mice of the C57/B6 strain were injected intradermally in the tail at two week intervals with 100 µg naked DNA purified from a CDM8 ova plasmid (described in detail in Shastri, et al., *J. Immunol.*, 150:2724–2736, 1993). The CDM8 ova plasmid contains the full length (1.8 kb) cDNA for ovalbumin.

2 weeks after the second gene adminstration, the spleens of the mice were removed and cultured in vitro with lethally irradiated (3000 rad) syngeneic splenocytes that had been pulsed with a synthetic ovalbumin peptide (SIIMFEKL). This peptide is a class I restricted target for cytotoxic T cells in mice with the histocompatibility haplotype $K^b$ described by Shastri, et al..

After five days of culture, the cells were incubated with targets of 2 types to test for the generation of cytotoxic T cells by the mice who had received the gene encoding ovalbumin. The targets were mouse EL-4 lymphocytes pulsed with the synthetic ovalbumin peptide, or EL-4 cells that had been stably transfected with the cDNA for ovalbumin (see, FIG. 11; the cDNA for ovalbumin is designated as "EG7" in the FIGURE). The percent lysis of the 2 targets was determined for different effector-to-target ratios (designated as "E:T ratio" in FIG. 11). As shown in FIG. 11, the animals that received the naked CDM8 ova plasmid had produced cytotoxic T cells that were specific for the ovalbumin targets (i.e., for EL-4 with the ovalbumin peptide and for EG7), but were not specific for the control EL-4 cells (i.e., those without the ovalbumin peptide).

C57/B6 mice vaccinated intradermally with CDM8 ova plasmids were also screened for antibodies to ovalbumin. Sera collected 6 weeks after administration of the CDM8 ova plasmids did not contain any detectable levels of antibody (as measured using an enzyme-linked immunoabsorbent assay on microtiter plates coated with ovalbumin; see, FIG. 12). Collectively, these data indicate that the methods for administration of naked polynucleotides of the invention will induce MHC class I restricted cytotoxic T cells (here, to ovalbumin) without inducing antibody production.

EXAMPLE X

PROLONGED IMMUNOLOGIC MEMORY AFTER INTRADERMAL ADMINISTRATION OF NAKED POLYNUCLEOTIDES INDUCED BY ANTIGEN STIMULATION OF T CELLS 0.1, 1, 10 and 100 µg of naked polynucleotides in plasmid form (0.5–5 ng/1 mg DNA endotoxin content) encoding the *E. coli* enzyme β-galactosidase under the control of the CMV promoter ("pCMV Lac-Z") were administered to groups of 4 mice/dosage/route either intramuscularly ("IM") or intradermally ("ID"). For comparison, another group of 4 mice/dosage received 100 µg β-galactosidase protein ("PR") intradermally. All injections were made using 50 µl normal saline as carrier. IM and ID injections were made with a 0.5 ml syringe and a 28.5 gauge needle. Antibodies were thereafter measured by enzyme-linked immunoabsorbent assay at 2 week intervals.

Briefly, total antibodies were measured using β-galactosidase (Calbiochem, Calif.) as the solid phase antigen. Microtiter plates (Costar, Cambridge, Mass.) were coated with 5 µg of antigen dissolved in 90 mM borate (pH 8.3) and 89 mM NaCl (i.e., borate buffered saline; BBS) overnight at room temperature and blocked overnight with 10 mg/ml of bovine serum albumin in BBS.

Serum samples were serially diluted in BBS starting at a 1:40 dilution for the first 8 weeks, them a 1:320 dilution thereafter. These samples were added to the plates and stored overnight at room temperature. Plates were washed in BBS+ 0.05% polysorbate 20, then reacted with a 1:2000 dilution of alkaline phosphatase labeled goat anti-mouse IgG antibody (Jackson Immunoresearch Labs., West Grove, Pa.) for 1 hour at room temperature, or were reacted with a 1:2000 dilution of alkaline phosphatase labeled goat anti-mouse IgG 1 antibody (Southern Biotech of AL), or were reacted with a 1:500 dilution of alkaline phosphatase labled rat anti-mouse IgG 2A antibody (Pharmingen, of CA), under the same conditions. Plates were washed again, then a solution of 1 mg/ml of p-nitrophenol phosphate (Boehringer-Mannheim, Indianapolis, IN) in 0.05M carbonate buffer (pH 9.8), containing 1 mM $MgCl_2$ was added. Absorbance at 405 nm was read 1 hour after addition of substrate to the plates.

Figure 13:
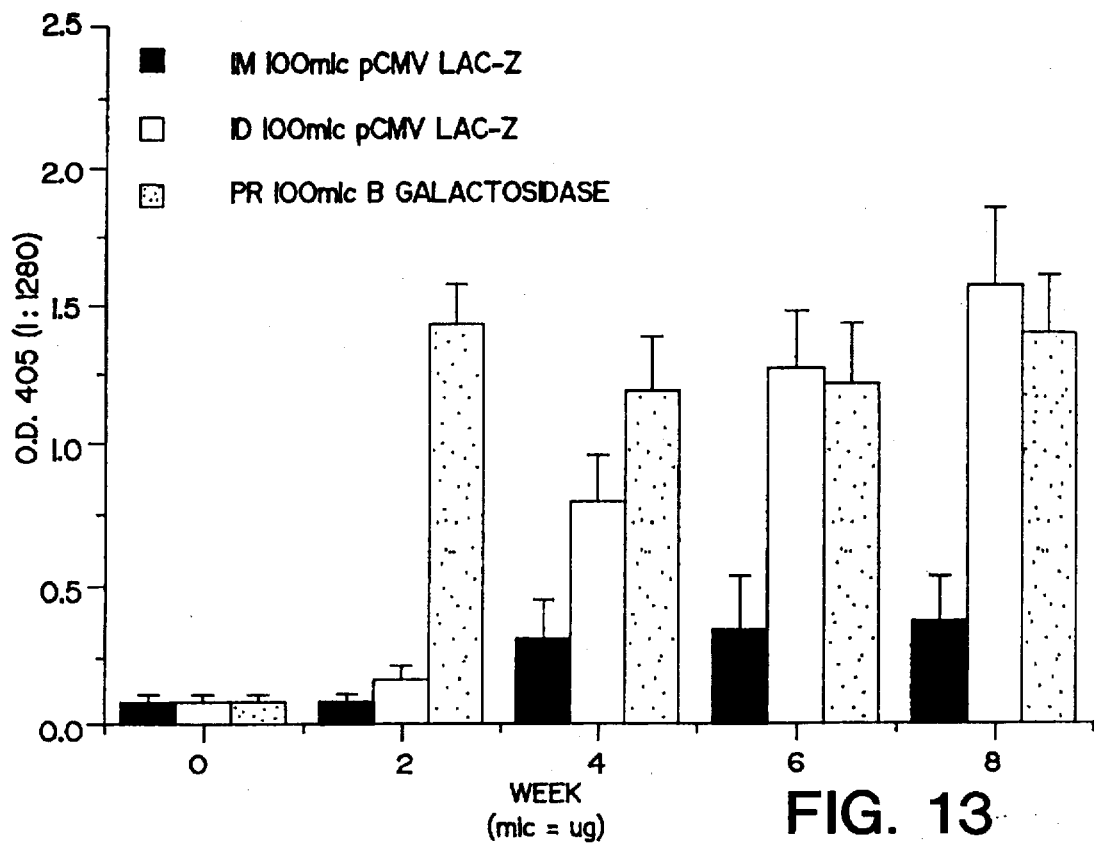
FIG. 13 depicts the results of an ELISA for anti-β-galactosidase antibodies after administration of (1) a polynucleotide encoding the enzyme by intramuscular or intradermal injection, and (2) the enzyme by intradermal injection.

As shown in FIG. 13, antibody responses of equivalent magnitude were induced in the animals who had received the pCMV Lac-Z plasmids by ID injection and the animals who had received the PR, while lesser antibody responses were measured in the animals who had received the pCMV Lac-Z plasmids by IM injection.

To assess for T cell memory, the animals were then boosted with 0.5 µg of PR at a separate site by ID injection. If these animals had developed memory T cells to control production of antibody to β-galactosidase, they would be expected to mount a more vigorous immune response after boosting with soluble protein antigen than had been demonstrated in response to the priming dose of antigen.

Figure 14:
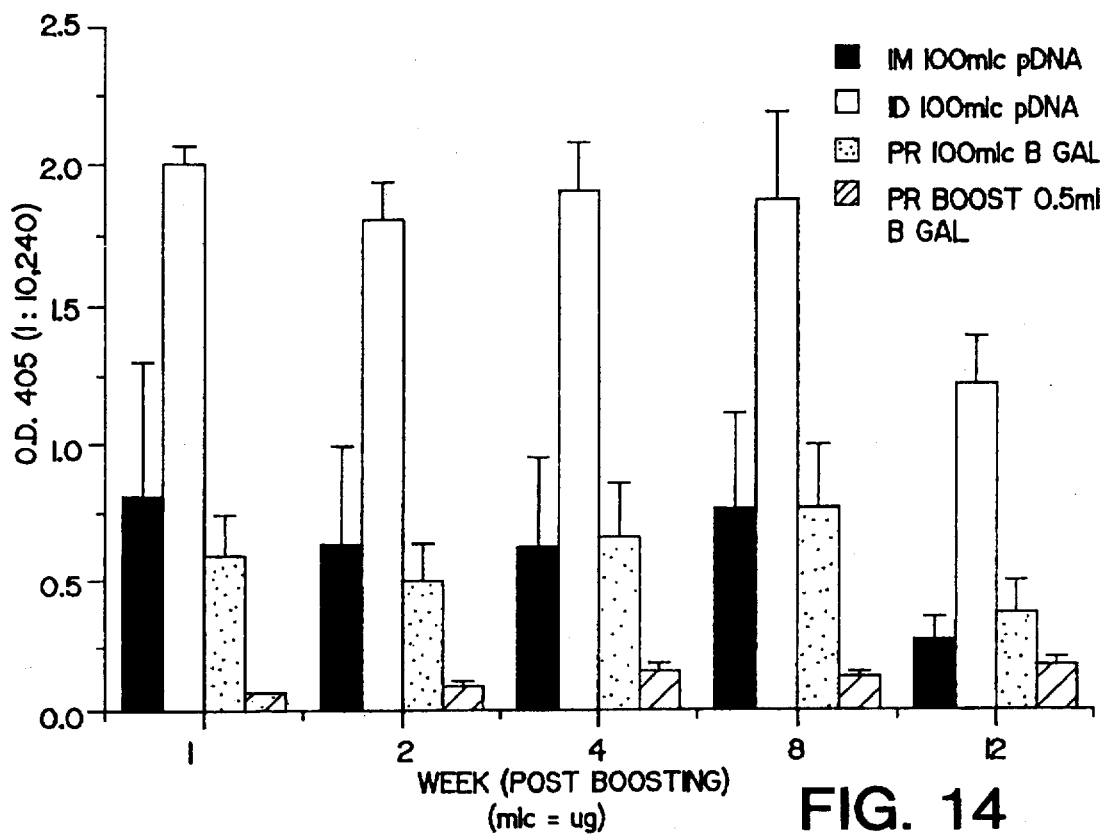
FIG. 14 depicts the results of an ELISA for anti-β-galactosidase antibodies in sera from the mice described with respect to FIG. 13 after a booster injection of antigen.

As shown in FIG. 14, it is clear that the animals which had received ID injections of pCMV Lac-Z plasmid had developed substantially better immunological memory than did animals which had received either IM injections of plasmid or of PR. Further, the memory which was developed by the ID injected animals persisted for a minimum of about 12 weeks.

EXAMPLE XI

SELECTIVE INDUCTION OF A TH1 RESPONSE AFTER INTRADERMAL ADMINISTRATION OF NAKED POLYNUCLEOTIDES

In mice, IgG 2A antibodies are serological markers for a TH1 type immune response, whereas IgG 1 antibodies are indicative of a TH2 type immune response. TH2 responses include the allergy-associated IgE antibody class; soluble protein antigens tend to stimulate relatively strong TH2 responses. In contrast, TH1 responses are induced by antigen binding to macrophages and dendritic cells. TH1 responses are to be of particular importance in the treatment of allergies and AIDS.

To determine which response, if any, would be produced by mice who received naked polynucleotides according to the invention, mice were vaccinated with pCMV Lac-Z or protein as described in the preceding example. At 2 week intervals, any IgG 2a and IgG 1 to β-galactosidase were measured by enzyme-linked immunoabsorbent assay (using antibodies specific for the IgG 1 and IgG 2A subclasses) on microtiter plates coated with the enzyme.

Figure 15:
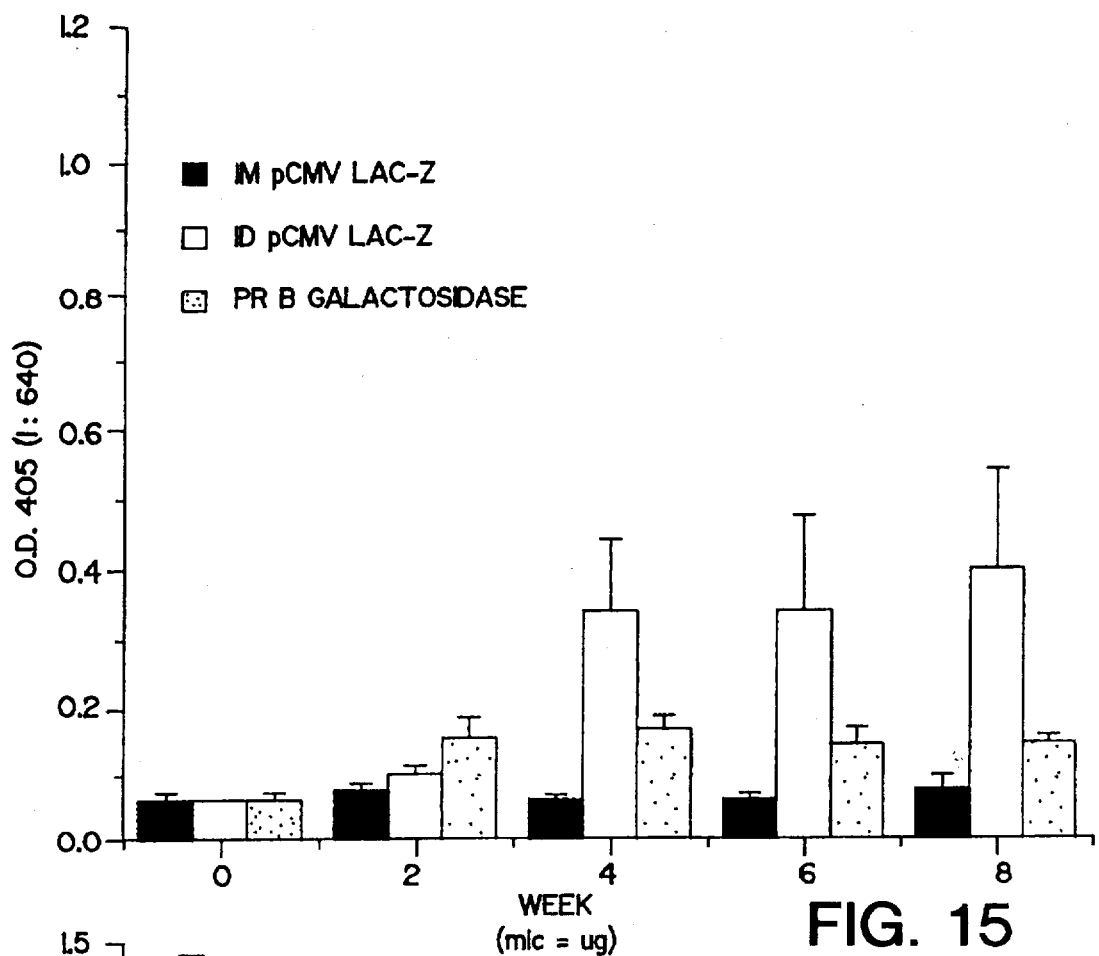
FIG. 15 depicts the results of an ELISA for IgG 2A type antibodies in sera for mice (1) injected intradermally or intramuscularly with a polynucleotide encoding β-galactosidase, or (2) the enzyme by intradermal injection.
Figure 16:
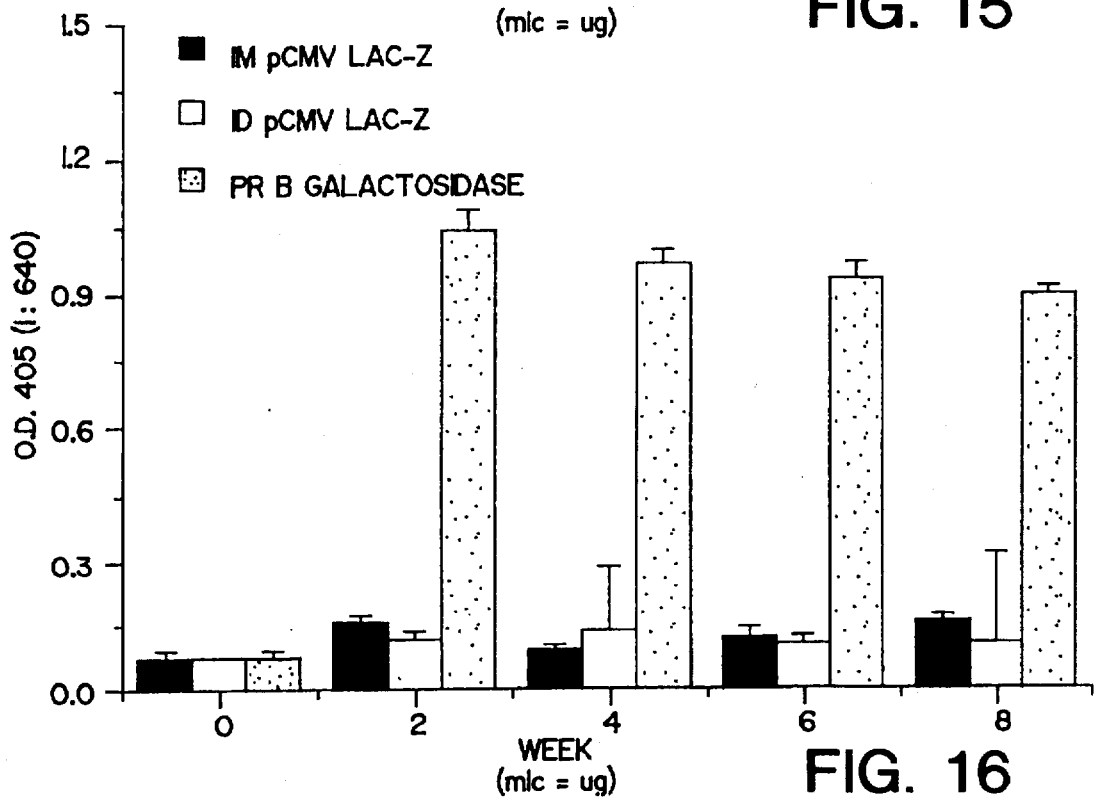
FIG. 16 depicts the results of an ELISA for IgG 1 type antibodies in sera for mice (1) injected intradermally or intramuscularly with a polynucleotide encoding β-galactosidase, or (2) the enzyme by intradermal injection.

As shown in FIG. 15, only the mice who received the plasmid by ID injection produced high titers of IgG 2A antibodies. As shown in FIG. 16, immunization of the mice with the enzyme itself ("PR") induced production of relatively high titers of IgG 1 antibodies. In the IM injected mice, low titers of both IgG 2A and IgG 1 antibodies were produced without apparent selectivity. The data shown in the FIGURES comprise averages of the values obtained from each group of 4 mice.

Figure 17:
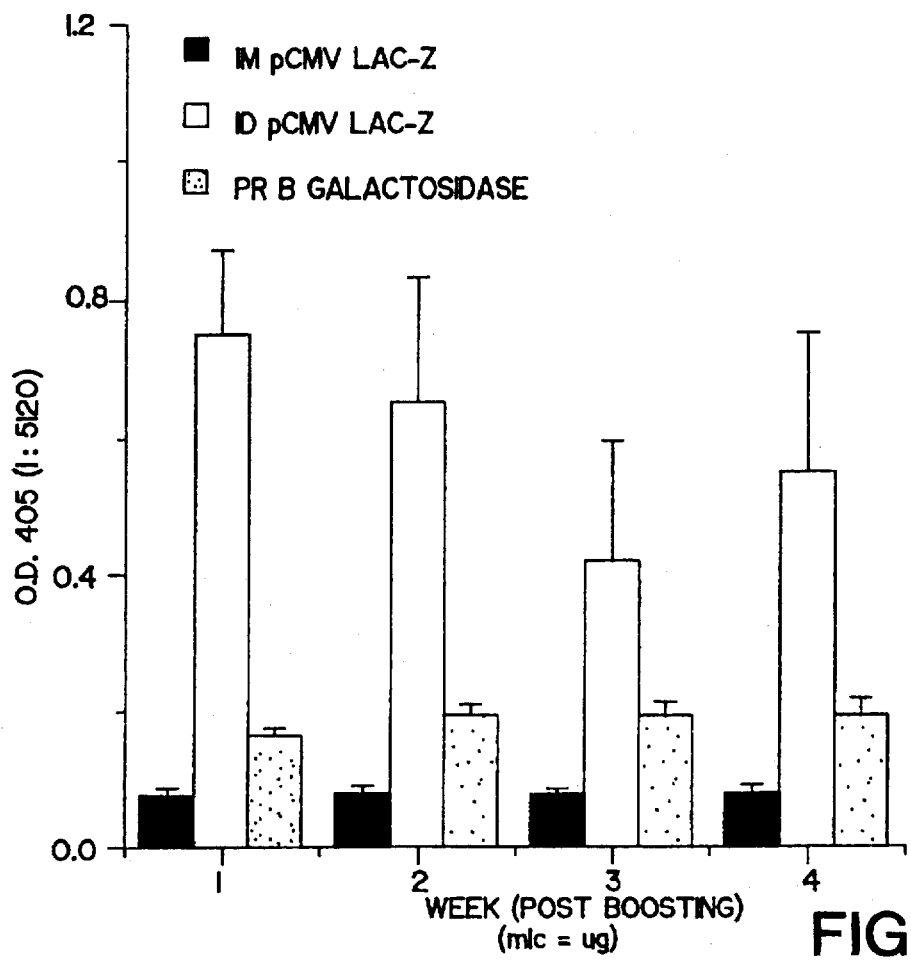
FIG. 17 depicts the results of an ELISA for IgG 2A type antibodies in sera of the mice described With respect to FIG. 25 after a booster injection of antigen.
Figure 18:
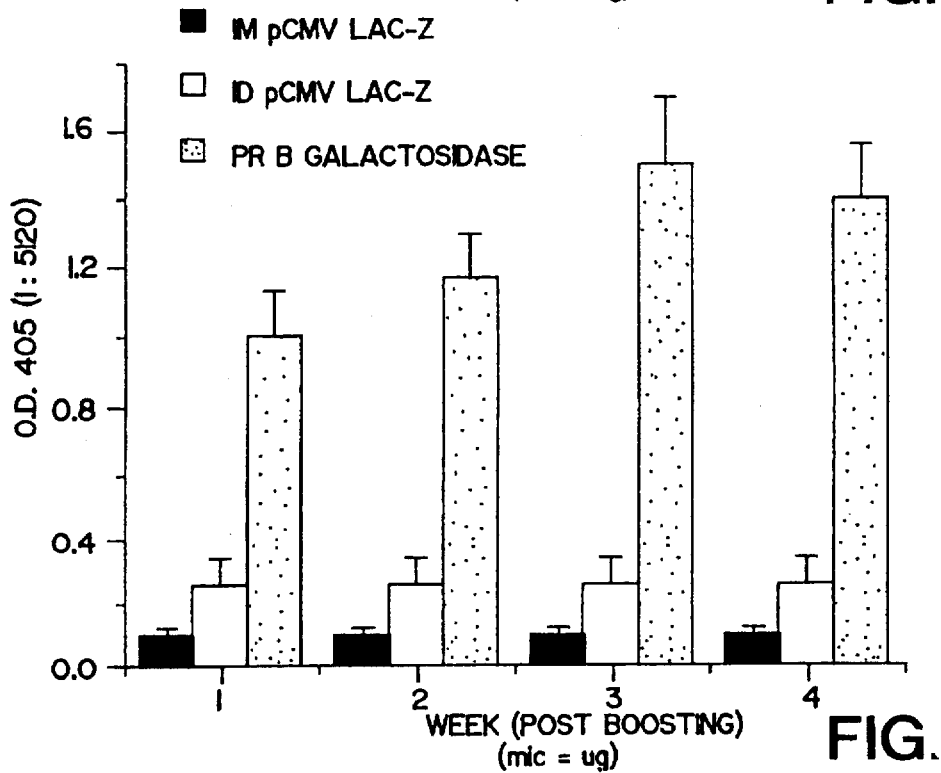
FIG. 18 depicts the results of an ELISA for IgG 1 type antibodies in sera of the mice described with respect to FIG. 24 after a booster injection of antigen.

To determine the stability of the antibody response over time, the same group of animals were boosted with 0.5 µg of enzyme injected intradermally. As shown in FIGS. 17 and 18 boosting of ID injection primed animals with the enzyme induced a nearly 10-fold rise in IgG 2A antibody responses (i.e., the antibody titer rose from 1:640 to 1:5120), but did not stimulate an IgG 1 response. These data indicate that the selective TH1 response induced by ID administration of naked polynucleotides is maintained in the host, despite subsequent exposure to antigen.

EXAMPLE XII

TH1 RESPONSES IN MICE AFTER ADMINISTRATION OF NAKED POLYNUCLEOTIDES WITH A MECHANICAL IRRITANT

The experiments described in Example XI were repeated in separate groups of mice, except that (1) only a priming dose was tested, and (2) the pCMV Lac-Z plasmid was administered to one group of 4 mice using the tyne device described in Example V, while β-galactosidase protein (10 μg) was administered to another group of 4 mice by intradermal (ID) injection.

Figure 19:
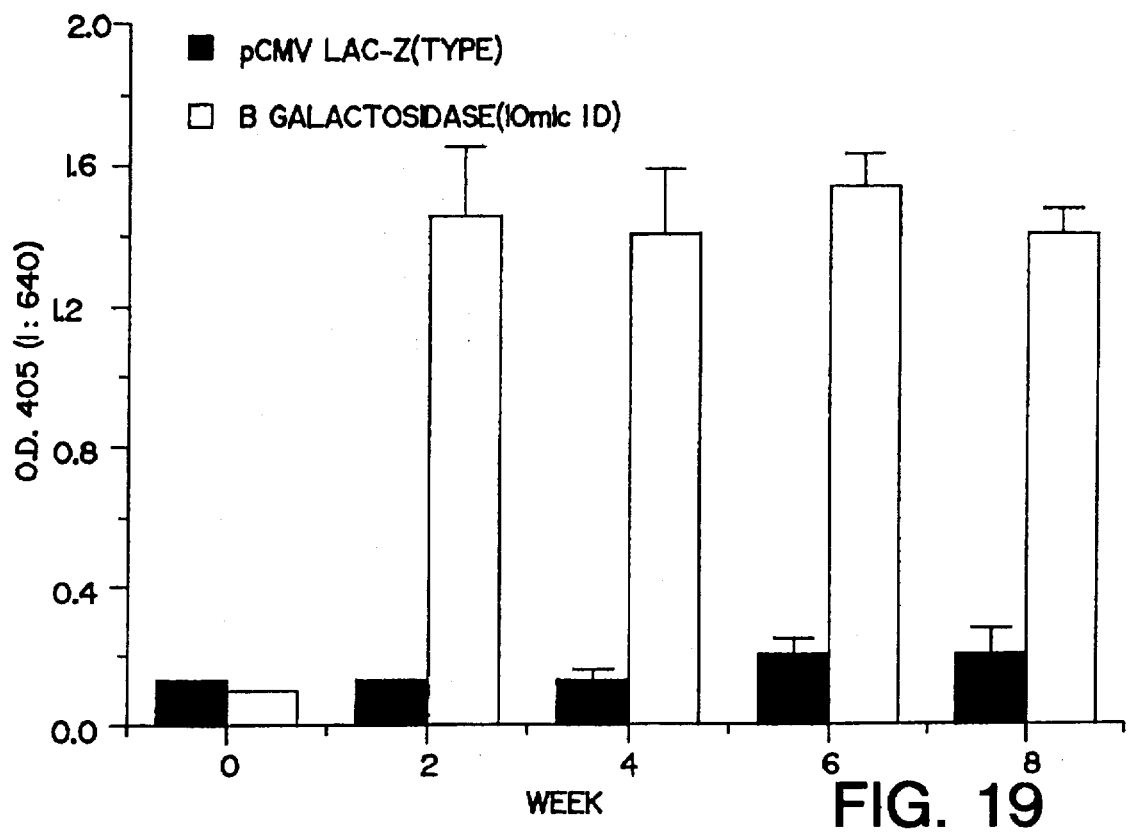
FIG. 19 depicts the results of an ELISA for IgG 1 type antibodies in sera for mice (1) introduced by scratching the skin with tynes coated with a polynucleotide encoding β-galactosidase, or (2) the enzyme by intradermal injection.
Figure 20:
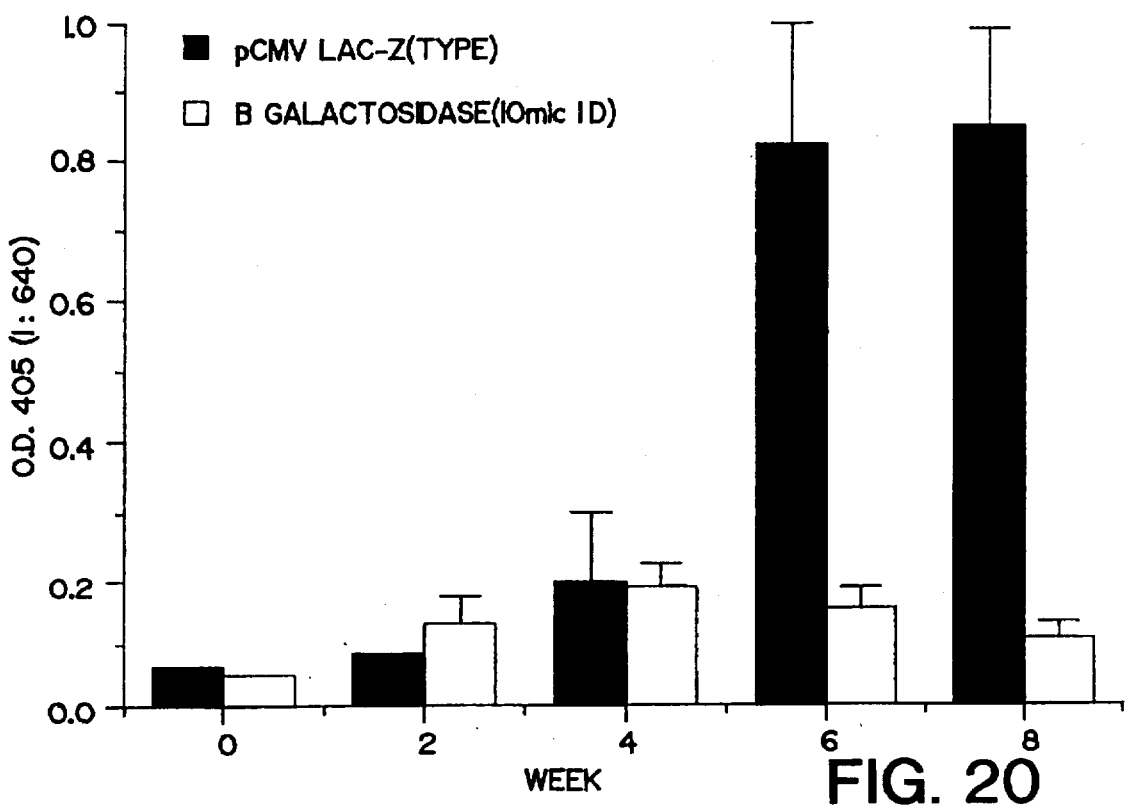
FIG. 20 depicts the results of an ELISA for IgG 2A type antibodies in sera for mice (1) introduced by scratching the skin with tynes coated with a polynucleotide encoding β-galactosidase, or (2) the enzyme by intradermal injection.

As shown in FIG. 19, the mice who received plasmid produced relatively low titers of IgG 1 antibody compared to the mice who received the protein. In contrast, as shown in FIG. 20, the mice who received plasmid produced substantially higher titers of IgG 2A antibody as compared to the mice who received the protein.

These results are similar to those obtained in Example XI except that, interestingly, the mice who received the plasmid via scratching of their skin with the tyne device produced even higher titers of IgG 2A antibody than did the mice who received the same plasmid via ID injection (both of which groups produced higher titers of IgG 2A antibody than did the mice who received the plasmid via IM injection). These results indicate that scratching of skin with the tyne device attracts greater number of APC's to the "injured" point of entry for the naked polynucleotides and are consistent with the theory that APC's are more efficient targets for gene administration and expression than are muscle or other somatic cells.

The data shown in the FIGURES comprise averages of the values obtained from each group of 4 mice.

EXAMPLE XIII

IL-4 AND INF$_\gamma$ LEVELS IN MICE AFTER IMMUNIZATION WITH ANTIGEN OR ANTIGEN-ENCODING POLYNUCLEOTIDES To confirm that the results shown by the data presented in Examples XI through XII can be attributed to the selective induction of TH1 responses (e.g., INF$_\gamma$ secretion) in plasmid injected mice, levels of IL-2 (indicative of a TH2 responses) and INF$_\gamma$ were assayed in the sera of the plasmid and protein injected mice of Example XI, after one booster injection of antigen. IL-2 levels were assayed as described in Example I; INF$_\gamma$ levels were assayed with an anti-INF$_\gamma$ murine antibody assay (see, e.g., Coligan, "Current Protocols in Immunology", Unit 6.9.5., Vol. 1, Wiley & Sons, 1994).

Figure 23:
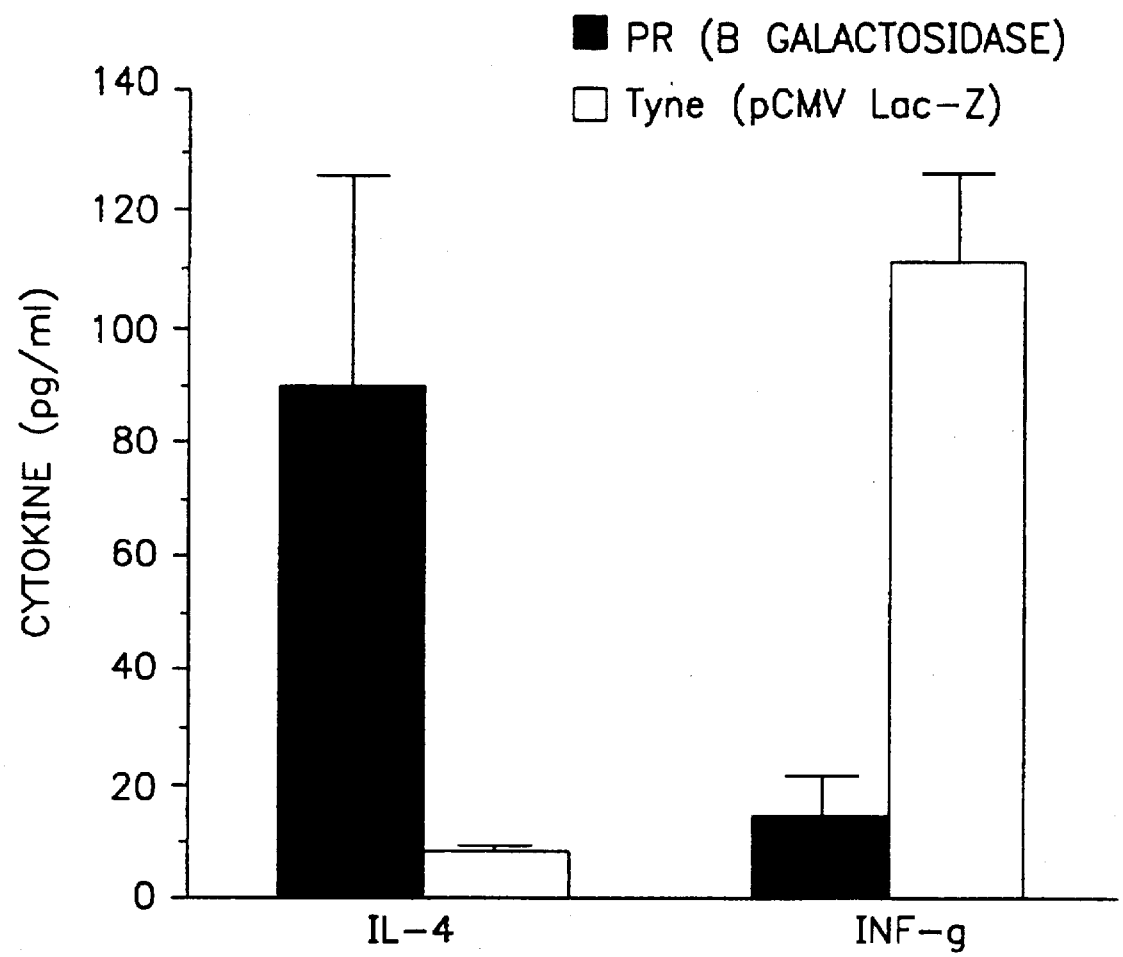
FIG. 23 depicts the results of an ELISA for levels of IL-2 and $INF_\gamma$ after immunization of mice with an antigen-encoding plasmid (pCMV-Lac-Z) or the antigen itself ((β galactosidase).

As shown in FIG. 23, levels of IL-4 in the protein injected mice were substantially higher than in plasmid injected mice (by about a 9:1 ratio). Conversely, levels of INF$_\gamma$ in the plasmid injected mice were substantially higher than in the protein injected mice (by a ratio of about 11:1).

EXAMPLE XIV

IN VIVO PRODUCTION AND MAINTENANCE OF CYTOTOXIC T LYMPHOCYTES AFTER IMMUNIZATION WITH ANTIGEN OR ANTIGEN-ENCODING POLYNUCLEOTIDES

To confirm whether the plasmid injected mice developed CTL's and maintained the anti-antigen protection afforded thereby, CTL levels in plasmid injected and control mice were measured.

The mice were immunized as described in Example V, except that they received pCMV-NP (described in Example I) rather than ovalbumin DNA. Control mice received pCMV-BL (a plasmid with a non-encoding insert). The total amount of pDNA loaded on the tyne device per inoculation was 50 μg of pCMV-NP and 25 μg of pCMV-BL.

36 weeks after immunization, the mice were sacrificed and splenocytes were removed for use in standard mixed lymphocyte cultures. The cultures were grown in the presence of a known synthetic peptide representing the major H-2$^d$ restricted CTL epitope of the NP protein. The cultures were assayed for anti-NP CTL activity 5–6 days later using NP peptide pulsed syngeneic P815 tumor cells (ATCC #TIB64, Rockville, Md.) as targets.

Figure 24:
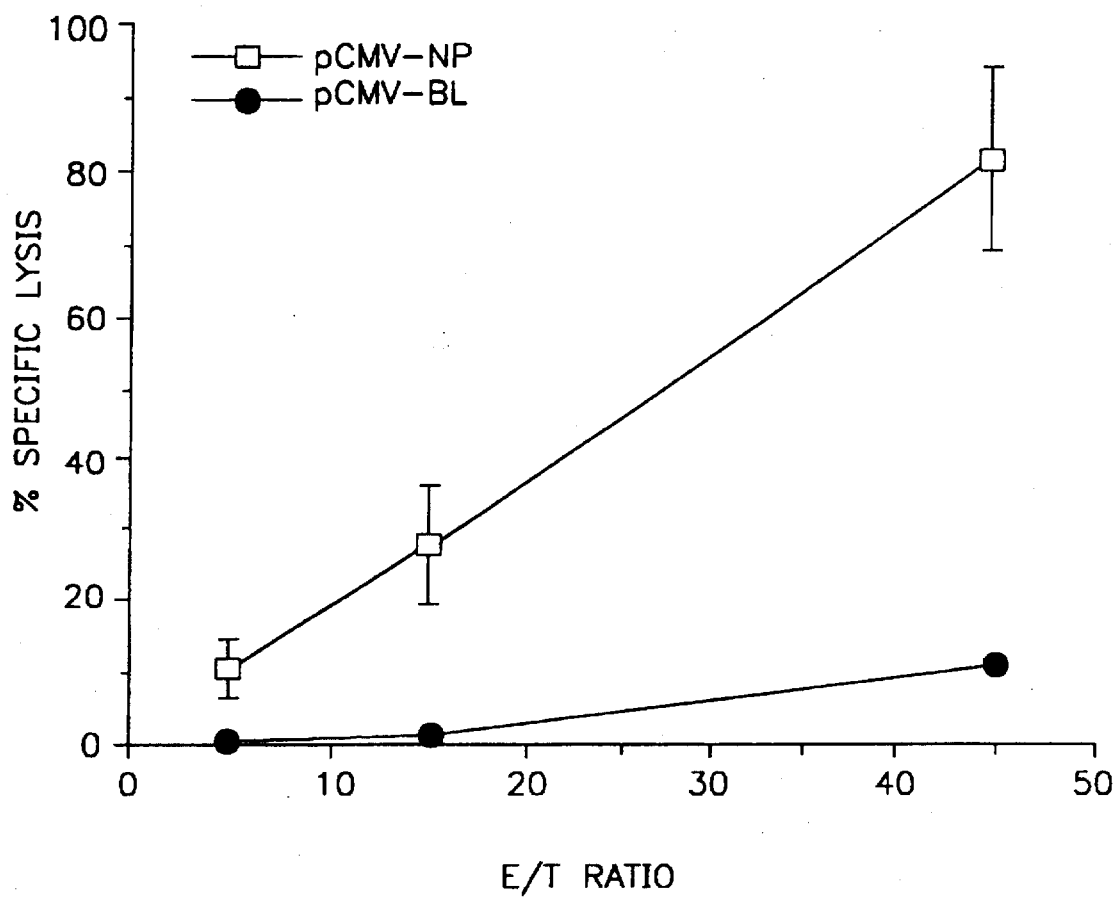
FIG. 24 depicts the results of an assay to detect antigen-specific cell lysis by T lymphocytes from mice immunized by epidermal administration of pCMV-NP plasmid.
Figure 25:
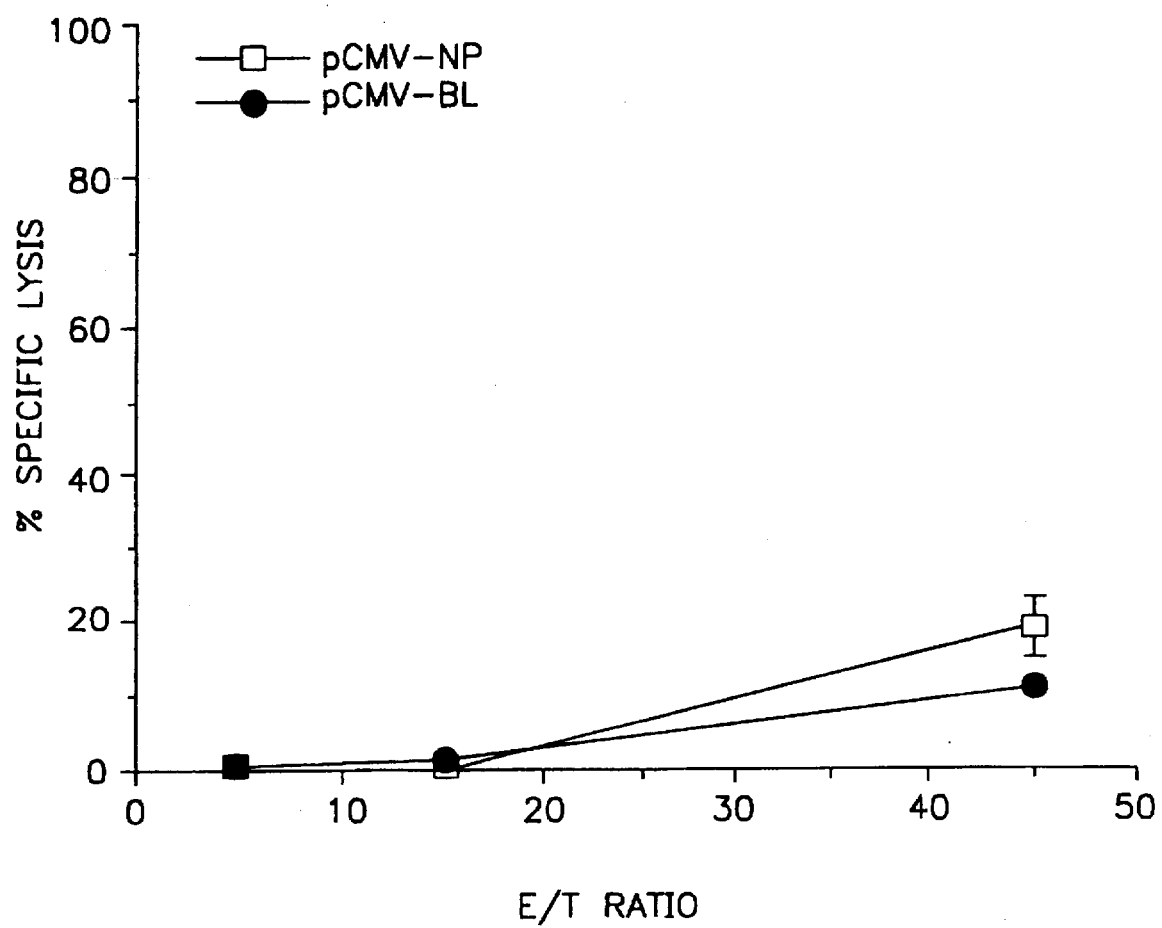
FIG. 25 depicts the results of an assay to detect antigen-specific cell lysis by T lymphocytes from the mice described in FIG. 24 in absence of pulsing of the cells with the antigen.

As shown in FIG. 24, mixed lymphocyte cultures prepared from the pCMV-NP injected animals displayed high levels of specific anti-NP cytolytic activity, reaching 10%, 30% and 80% of specific lysis at an effector to target (E/T) ratio of 5:1, 15:1 and 45:1, respectively. Control mice only displayed 1%, 1% and 9% under the same conditions. Further, in absense of exposure to the H-2$^d$ epitope peptide, there were not significant differences in CTL activity in the pCMV-NP injected and control mice (FIG. 25). These data indicate selective activation of TH1 cells in the pCMV-NP injected mice.

We claim:

1. A method for stimulating cytotoxic T lymphocytes reactive with tumor-associated antigen present on tumor cells in a mammalian host, comprising:

administering a naked polynucleotide to the skin or mucosa of the host, wherein the skin and mucosa have a high concentration of resident antigen presenting cells relative to other host tissues, wherein the naked polynucleotide operatively encodes for a therapeutically effective homologous or heterologous tumor-associated antigen mimic that will bind class I MHC molecules on antigen presenting cells; and, wherein the antigen mimic is expressed in the antigen presenting cells without substantial secretion therefrom and is presented by the cells to stimulate cytotoxic T lymphocytes to lyse tumor cells in the host which bear the tumor-associated antigen.

2. The method according to claim 1 wherein the tumor cells are present in the skin or mucosa of the host.

3. The method according to claim 1 wherein the naked polynucleotide is coated onto the tynes of a multiple tyne device and is administered by penetrating the skin or mucosa of the host with the tynes.

4. The method according to claim 1 wherein the naked polynucleotide is under the control of a nuclear receptor promoter.

5. The method according to claim 4 wherein the promoter is activated by application of an activating ligand specific for the nuclear receptor to the skin or mucosa of the host at the point of entry of the polynucleotide.

6. The method according to claim 5 wherein the ligand is selected from the group consisting of 1,25-dihydroxyvitamin D$_3$, steroid hormones, thyroid hormone and retinoids.

7. The method according to claim 1 wherein the tumor cells are residual tumor cells left in the host after removal of an organ having the tumor cells present therein.

8. The method according to claim 1 wherein the host is co-immunized with polynucleotides which encode homologous tumor-associated antigens and with polynucleotides which encode heterologous tumor-associated antigens.

9. The method according to claim 1 wherein the host is co-immunized with the tumor-associated antigen.

10. The method according to claim 1 wherein the host is co-immunized with a naked polynucleotide which operatively encodes an immunostimulatory cytokine.

11. The method according to claim 1 wherein presentation of the antigen mimic activates Th1 lymphocytes in preference to Th2 lymphocytes in the host, thus reducing antigen-stimulated release of IgE antibody and the concomitant risk of anaphylaxis.

* * * * *

UNITED STATES PATENT AND TRADEMARK OFFICE
CERTIFICATE OF CORRECTION

PATENT NO. : 5,679,647
DATED : Oct. 21, 1997
INVENTOR(S) : Carson, et al.

It is certified that error appears in the above-indentified patent and that said Letters Patent is hereby corrected as shown below:

At Col. 2, line 15, "mica" should be --mice--.
At Col. 2, line 53, "tbat" should be --that--.
At Col. 7, line 27, "immunogeneity" should be --immunogenicity--.
At Col. 10, line 24, "arrows" should be --arrow--.
At Col. 3, line 49, "allergen" should be --cancer--.

IN THE CLAIMS:

The claims should read as follows:

1. A method for stimulating cytotoxic T lymphocytes reactive with tumor-associated antigen present on tumor cells in a mammalian host, comprising:

administering a naked polynucleotide to the skin of the host, wherein the skin has a high concentration of resident antigen presenting cells relative to other host tissues, wherein the naked polynucleotide operatively encodes for a therapeutically effective homologous or heterologous tumor-associated antigen mimic that will bind class I MHC molecules on antigen presenting cells; and, wherein the antigen mimic is expressed in the antigen presenting cells without substantial secretion therefrom and is presented by the cells to stimulate cytotoxic T lymphocytes to lyse tumor cells in the host which bear the tumor-associated antigen.

UNITED STATES PATENT AND TRADEMARK OFFICE
CERTIFICATE OF CORRECTION

PATENT NO. : 5,679,647
DATED : Oct. 21, 1997
INVENTOR(S) : Carson, et al.

It is certified that error appears in the above-indentified patent and that said Letters Patent is hereby corrected as shown below:

2. The method according to Claim 1 wherein the tumor cells are present in the skin of the host.

3. The method according to Claim 1 wherein the naked polynucleotide is coated onto the tynes of a multiple tyne device and is administered by penetrating the skin of the host with the tynes.

4. The method according to Claim 1 wherein the naked polynucleotide is under the control of a nuclear receptor promoter.

5. The method according to Claim 5 wherein the promoter is activated by application of an activating ligand specific for the nuclear receptor to the skin of the host at the point of entry of the polynucleotide.

6. The method according to Claim 6 wherein the ligand is selected from the group consisting of 1,25-dihydroxyvitamin $D_3$, steroid hormones, thyroid hormone and retinoids.

7. The method according to Claim 1 wherein the tumor cells are residual tumor cells left in the host after removal of an organ having the tumor cells present therein.

8. The method according to Claim 1 wherein the host is co-immunized with polynucleotides which encode homologous tumor-associated antigens and with polynucleotides which encode heterologous tumor-associated antigens.

9. The method according to Claim 1 wherein the host is co-immunized with the tumor-associated antigen.

UNITED STATES PATENT AND TRADEMARK OFFICE
CERTIFICATE OF CORRECTION

PATENT NO. : 5,679,647
DATED : Oct. 21, 1997
INVENTOR(S) : Carson, et al.

Page 3 of 5

It is certified that error appears in the above-indentified patent and that said Letters Patent is hereby corrected as shown below:

10. The method according to Claim 1 wherein the host is co-immunized wtih a naked polynucleotide which operatively encodes an immunostimulatory cytokine.

11. The method according to Claim 1 wherein presentation of the antigen mimic activates Th1 lymphocytes in preference to Th2 lymphocytes in the host, thus reducing antigen-stimulated release of IgE antibody and the concomitant risk of anaphylaxis.

12. A method for stimulating cytotoxic T lymphocytes reactive with tumor-associated antigen present on tumor cells in a mammalian host, comprising:

administering a naked polynucleotide to the skin [or mucosa] of the host, wherein the skin has a high concentration of resident antigen presenting cells relative to other host tissues, wherein the naked polynucleotide operatively encodes for a therapeutically effective homologous or heterologous tumor-associated antigen mimic that will bind class I MHC molecules on antigen presenting cells; and, wherein the antigen mimic is expressed in the antigen presenting cells without substantial secretion therefrom and is presented by the cells to stimulate cytotoxic T lymphocytes to lyse tumor cells in the host which bear the tumor-associated antigen.

UNITED STATES PATENT AND TRADEMARK OFFICE
CERTIFICATE OF CORRECTION

PATENT NO. : 5,679,647
DATED : Oct. 21, 1997
INVENTOR(S) : Carson, et al.

It is certified that error appears in the above-indentified patent and that said Letters Patent is hereby corrected as shown below:

13. The method according to Claim 15 wherein the tumor cells are present in the mucosa of the host.

14. The method according to Claim 15 wherein the naked polynucleotide is coated onto the tynes of a multiple tyne device and is administered by penetrating the mucosa of the host with the tynes.

15. The method according to Claim 15 wherein the naked polynucleotide is under the control of a nuclear receptor promoter.

16. The method according to Claim 18 wherein the promoter is activated by application of an activating ligand specific for the nuclear receptor to the mucosa of the host at the point of entry of the polynucleotide.

17. The method according to Claim 19 wherein the ligand is selected from the group consisting of 1,25-dihydroxyvitamin $D_3$, steroid hormones, thyroid hormone and retinoids.

18. The method according to Claim 15 wherein the tumor cells are residual tumor cells left in the host after removal of an organ having the tumor cells present therein.

UNITED STATES PATENT AND TRADEMARK OFFICE
CERTIFICATE OF CORRECTION

PATENT NO. : 5,679,647
DATED : Oct. 21, 1997
INVENTOR(S) : Carson, et al.

It is certified that error appears in the above-indentified patent and that said Letters Patent is hereby corrected as shown below:

19. The method according to Claim 15 wherein the host is co-immunized with polynucleotides which encode homologous tumor-associated antigens and with polynucleotides which encode heterologous tumor-associated antigens.

20. The method according to Claim 15 wherein the host is co-immunized with the tumor-associated antigen.

21. The method according to Claim 15 wherein the host is co-immunized wtih a naked polynucleotide which operatively encodes an immunostimulatory cytokine.

22. The method according to Claim 15 wherein presentation of the antigen mimic activates Th1 lymphocytes in preference to Th2 lymphocytes in the host, thus reducing antigen-stimulated release of IgE antibody and the concomitant risk of anaphylaxis.

Signed and Sealed this

Twenty-first Day of July, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO:     5,679,647
DATED:     October 21, 1997
INVENTOR(S):     Carson et al.

It is certified that error appears in the above-identified patent and that said Letters Patent are hereby corrected as shown below:

On the title page:

Please delete the Related U.S. Application Data [63] in its entirety and replace with:

-- Continuation-in-part of PCT Application No. US94/09661, filed August 25, 1994, which is a continuation-in-part of Ser. No. 112, 440, filed August 26, 1993, abandoned. --

Signed and Sealed this

Twenty-fourth Day of April, 2001

*Attest:*

NICHOLAS P. GODICI

*Attesting Officer*      Acting Director of the United States Patent and Trademark Office